(12) United States Patent
Brand et al.

(10) Patent No.: US 8,821,556 B2
(45) Date of Patent: Sep. 2, 2014

(54) SUPPORT AND MOUNTING FOR SURGICAL OBJECTS

(75) Inventors: Stefan Brand, Basel (CH); Dirk Thiel, Staufen (DE)

(73) Assignee: Medartis AG, Basel (CH)

(*) Notice: Subject to any disclaimer, the term of this patent is extended or adjusted under 35 U.S.C. 154(b) by 281 days.

(21) Appl. No.: 13/147,282

(22) PCT Filed: Feb. 25, 2010

(86) PCT No.: PCT/EP2010/052435
§ 371 (c)(1),
(2), (4) Date: Aug. 1, 2011

(87) PCT Pub. No.: WO2010/097447
PCT Pub. Date: Sep. 2, 2010

(65) Prior Publication Data
US 2011/0288596 A1    Nov. 24, 2011

(30) Foreign Application Priority Data
Feb. 26, 2009   (DE) .................... 20 2009 002 639 U

(51) Int. Cl.
A61B 17/04     (2006.01)
A61B 19/02     (2006.01)
A61B 17/86     (2006.01)
A61B 17/80     (2006.01)

(52) U.S. Cl.
CPC .............. *A61B 17/865* (2013.01); *A61B 17/80* (2013.01); *A61B 19/026* (2013.01); *A61B 19/0256* (2013.01)
USPC ............................ 606/301; 606/300; 206/438

(58) Field of Classification Search
USPC .................. 606/104, 328, 329; 206/339, 438
See application file for complete search history.

(56) References Cited

U.S. PATENT DOCUMENTS 5,215,726 A    6/1993   Kudla et al.
5,732,821 A    3/1998   Stone et al.
(Continued)

FOREIGN PATENT DOCUMENTS

BE    1005149 A6    3/1984
DE    807124         6/1951
(Continued)

*Primary Examiner* — Nicholas Woodall
(74) *Attorney, Agent, or Firm* — Shoemaker and Mattare

(57) ABSTRACT

The invention relates to a support (1) for receiving at least one surgical object, in particular at least one bone screw (2), in a receiving position (A). Said support (1) comprises at least one supporting surface (3) which is designed and arranged in such a manner that a supporting area (5) of the object can be brought into contact with the supporting surface (3) in the receiving position (A). Said object can be removed from the receiving position (A) in the direction of removal (E). The direction of removal (E) extends at an angle of a maximum 45°, preferably a maximum 20°, more particularly essentially parallel to a longitudinal axis (L) of the object housed in the receiving position (A). Said support (1) comprises at least one mounting surface (4) that can be moved in relation to the base body (23) and which is designed and arranged in such a manner that the object can be maintained by means of the mounting surface (4) in the receiving position (A), in particular in a clamped manner. The invention also relates to a mounting (26) for fixing a bone plate support (27) for a bone plate (28) to a base plate (29), a bone plate support (27) and a system comprising a mounting (26) and a unit (33) from a bone plate support (27) and a bone plate (28).

18 Claims, 24 Drawing Sheets

(56) References Cited

U.S. PATENT DOCUMENTS

| | | | |
|---|---|---|---|
| 6,164,442 | A | 12/2000 | Stravitz |
| 6,450,328 | B1 | 9/2002 | Machacek et al. |
| 7,066,341 | B1 | 6/2006 | Hartford |
| 7,350,643 | B2 | 4/2008 | Capanni et al. |
| 7,516,845 | B2 * | 4/2009 | Lang et al. .................... 206/438 |
| 8,061,517 | B2 * | 11/2011 | Loeffler et al. ............... 206/339 |
| 8,162,138 | B2 * | 4/2012 | Bettenhausen et al. ....... 206/339 |
| 2005/0034630 | A1 | 2/2005 | Jayaram |
| 2005/0218024 | A1 * | 10/2005 | Lang et al. .................... 206/438 |
| 2006/0006087 | A1 * | 1/2006 | Lin .............................. 206/347 |
| 2008/0016989 | A1 | 1/2008 | Walker |
| 2008/0230423 | A1 * | 9/2008 | Loeffler et al. ............... 206/438 |
| 2011/0071572 | A1 * | 3/2011 | Sixto et al. .................... 606/286 |
| 2011/0108446 | A1 * | 5/2011 | Bettenhausen et al. ....... 206/438 |

FOREIGN PATENT DOCUMENTS

| | | |
|---|---|---|
| DE | 20108390 | 9/2001 |
| DE | 202005010530 | 10/2005 |
| DE | 202007004638 | 7/2007 |
| DE | 102006036460 | 2/2008 |
| DE | 202007016144 | 3/2008 |
| EP | 1582169 | 10/2005 |
| EP | 1972290 | 9/2008 |
| WO | 01/49198 | 7/2001 |
| WO | 03/079918 | 10/2003 |
| WO | 2005/053753 | 6/2005 |
| WO | 2005/092231 | 10/2005 |
| WO | 2009/024189 | 2/2009 |

* cited by examiner

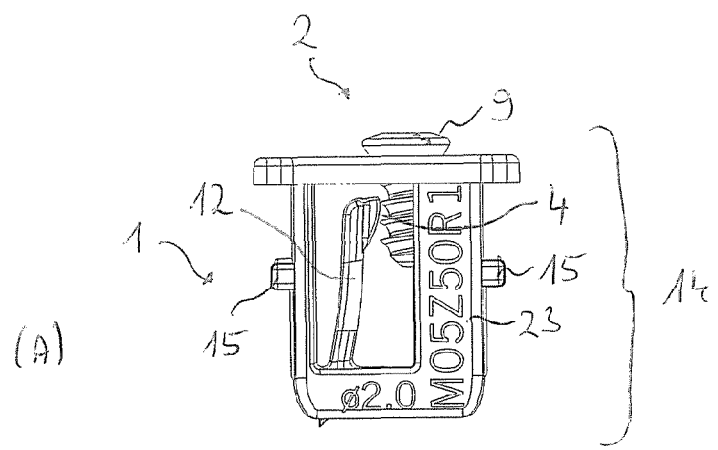
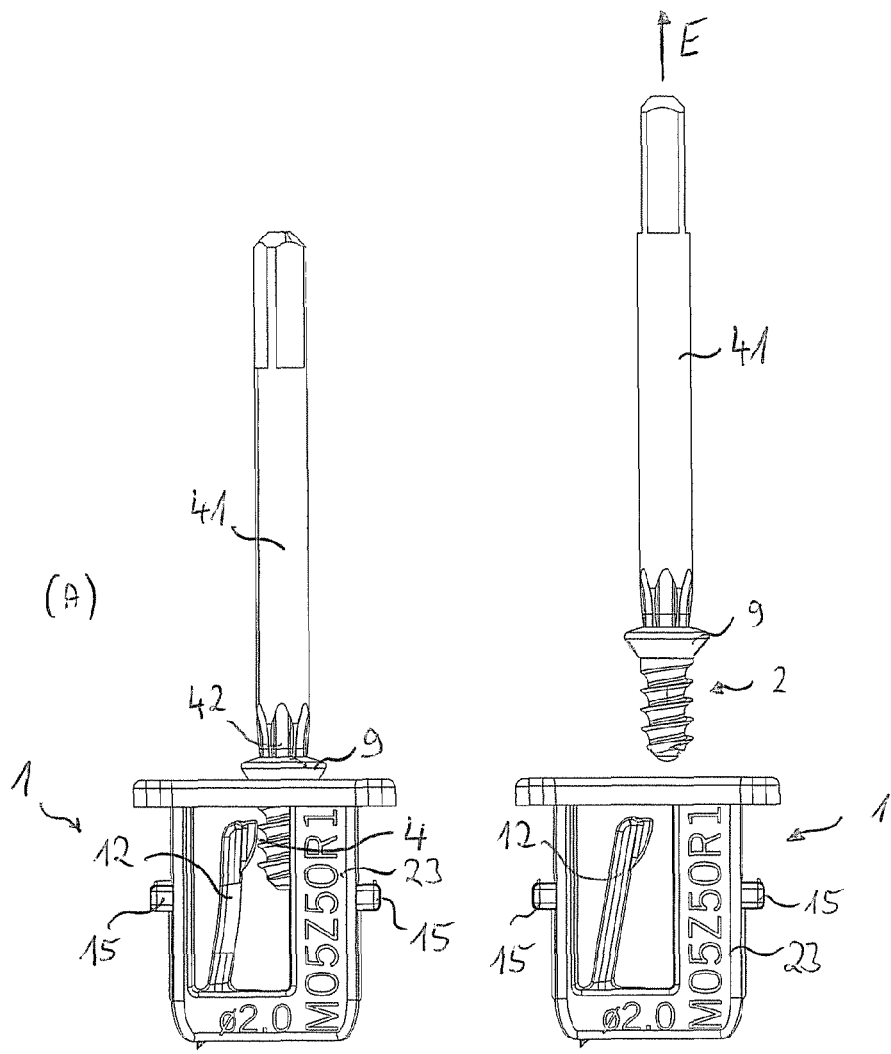
FIG. 9a
FIG. 9b  FIG. 9c

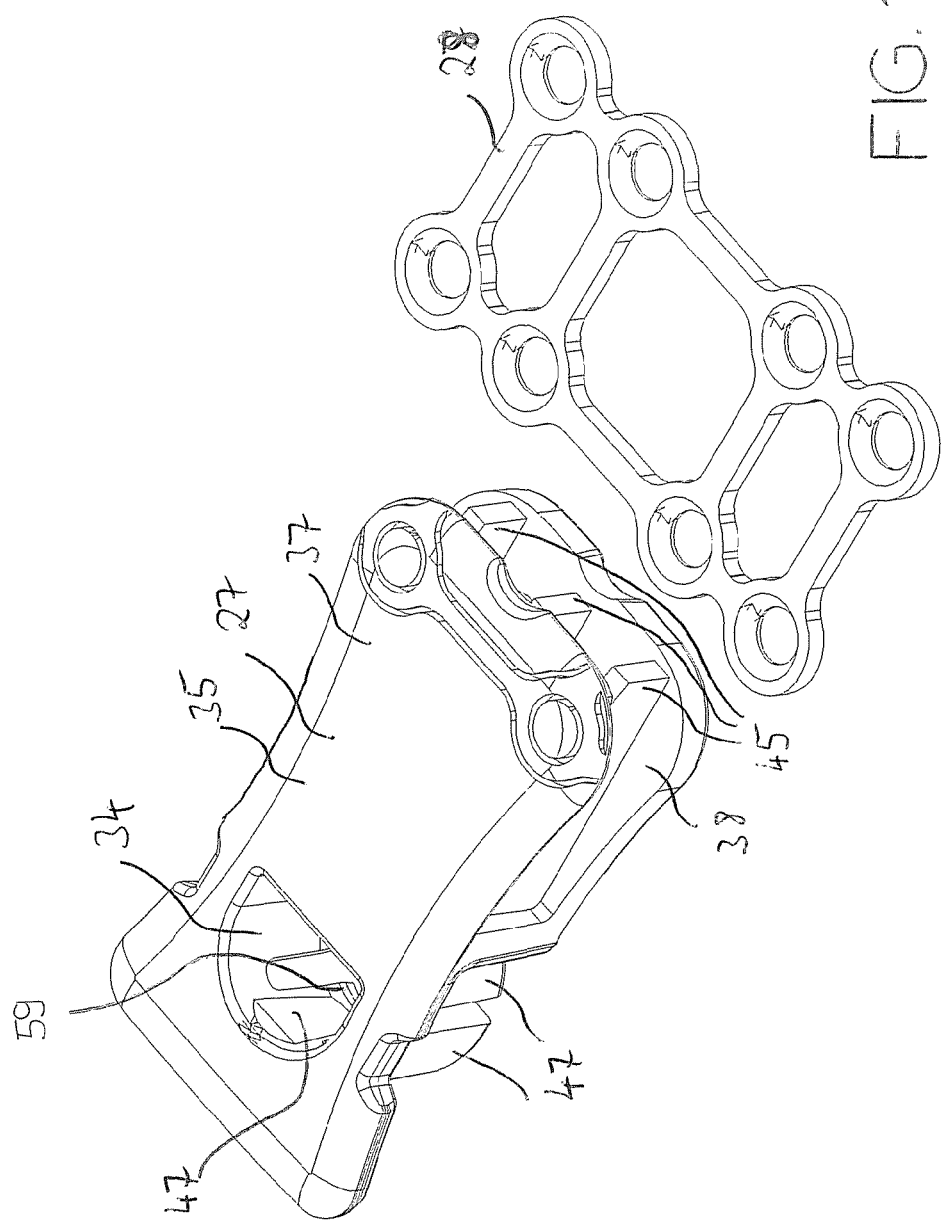

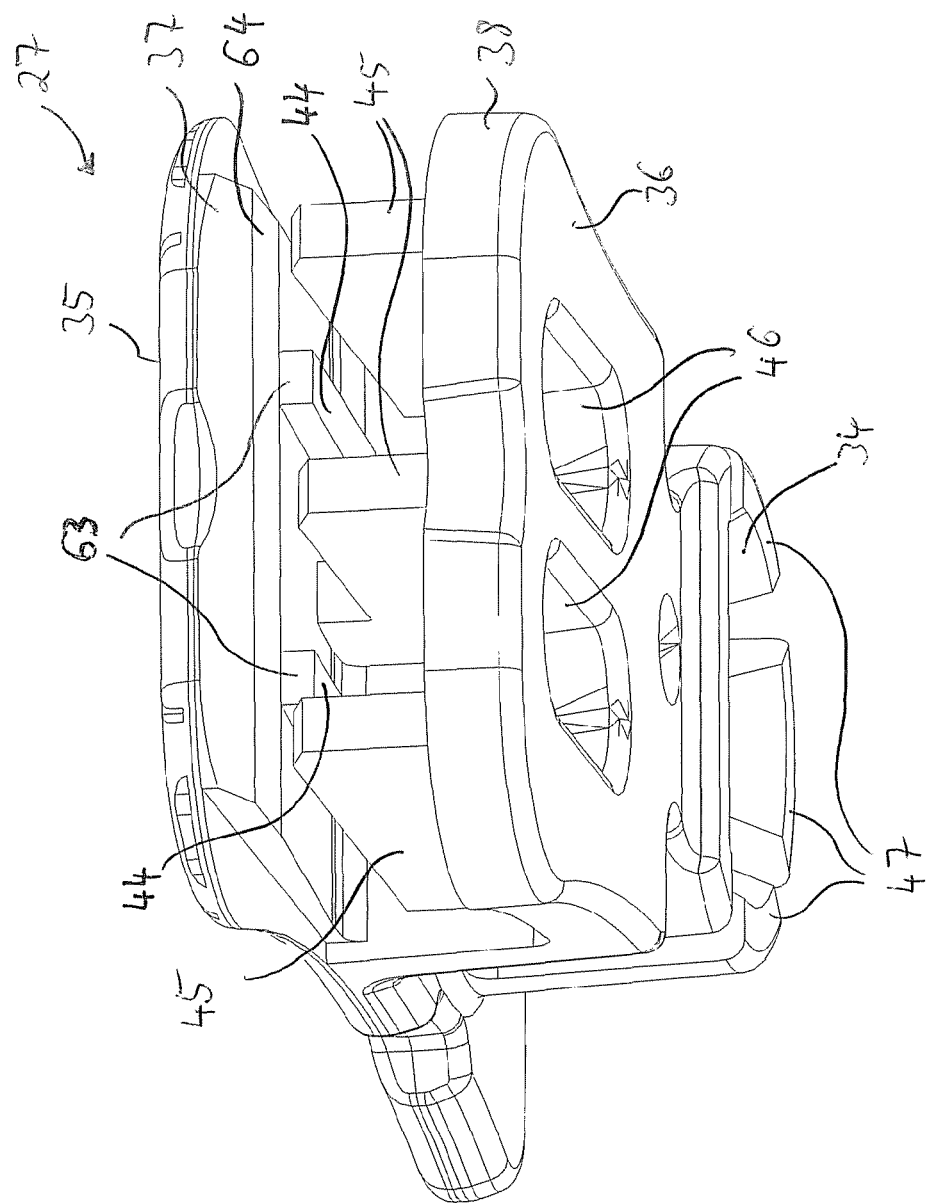

SUPPORT AND MOUNTING FOR SURGICAL OBJECTS

The present invention relates to supports for receiving at least one surgical object, a unit composed of such a support and of a surgical object, an osteosynthesis set, a mounting for fixing a surgical object, a bone plate support, and a system with a mounting and with a unit that comprises a bone plate support and a bone plate, according to the preambles of the independent claims.

In bone surgery, a large number of bone screws, bone nails and similar surgical objects are often needed and have to be available to the surgeon when so required during the operation. The often small dimensions of the bone screws, etc., make them very difficult to handle. In particular, it is difficult to grip small bone screws or the like with a hand and with a screwdriver.

A support according to the preamble of independent claim 1 is already known from WO 2005/092231, which support is suitable for the storage and presentation of an individual bone screw. The screw is fitted loosely in an opening of the support and therefore has to be secured by an additional cover against accidentally falling out.

This arrangement, however, has many disadvantages. For example, the screw is not visible when the cover is fitted, with the result, for example, that it is not possible to tell directly whether it is a Torx screw or a recessed head screw. Likewise, any inscription with length data on the upper face of the support cannot be seen when the cover is fitted. Moreover, the cover makes cleaning and sterilization of the screw head difficult and leads to an increased overall height. In addition, before the bone screw is removed, the cover has to be taken off separately, which constitutes another work step and thus makes handling during an operation more difficult. Furthermore, the bone screw can fall out of the support when the cover, in preparation for an operation, has already been taken off and the container containing the supports is accidentally tilted. A bone screw that has been accidentally removed or has fallen out of the support can also be fitted back into the support and, for example, accidentally used in a subsequent operation, which fails to meet the legal requirements. Moreover, a bone screw that has been removed or has fallen out of the support can be accidentally fitted into the wrong support, which can make identification of the bone screw difficult.

WO 01/49198 discloses an elastic support into which a bone screw can be clamped. This support allows the bone screw to be removed only transversely with respect to the longitudinal axis thereof. One or more such supports can be stored horizontally in a surgical container, such that the bone screw can be removed directly in a vertically upward direction. However, this increases the space taken up in the horizontal plane of the container. Alternatively, the supports could be stored upright. In this case, however, the support would first have to be taken out of the container before the bone screw can be removed, which makes handling slower and more difficult.

Finally, EP 1 972 290 discloses another support for a bone screw. The bone screw can be clamped with the aid of tongue-shaped holding elements. However, the supports disclosed therein permit a tilting movement of the bone screw, which stands in the way of secure storage. In addition, in this support too, the screw first has to be moved transversely with respect to its longitudinal direction in order to allow it to be removed from the support. This takes up more space, since the bone screw first has to be moved laterally. Moreover, the maneuver for removing the bone screw is quite awkward.

Some bone screws have a shank and, arranged on the latter, a cross-sectional enlargement. Intermaxillary fixation screws (IMF screws), which are known per se, may be mentioned by way of example. The cross-sectional enlargement can have a diameter that is only slightly smaller than or can even be greater than the diameter of the screw head. The above-described supports known from the prior art are not suitable for receiving and storing such screws. For example, in a support of the kind disclosed in WO 2005/092231, the bone screw would bear with the underside of the cross-sectional enlargement on the upper face of the bearing surface of the support. Consequently, the screw head would protrude well beyond the bearing surface, such that the cover would have to be made even larger.

It is an object of the present invention to overcome the disadvantages of what is known and, in particular, to make available a support for receiving at least one surgical object, in which the object can be held in a stable manner and from which it can be easily removed. In addition, the overall size of the support is to be kept as small as possible.

A first aspect of the invention concerns a support for receiving at least one elongate surgical object, which surgical object has a shank and, arranged on the shank, a cross-sectional enlargement. The elongate surgical object can be, for example, a bone screw or a bone nail. According to the invention, the support has holding means for holding the surgical object in the area of the cross-sectional enlargement of the shank thereof. In particular, the holding means can be designed for bracing and/or clamping the surgical object in the area of the cross-sectional enlargement.

By virtue of the hold in the area of the cross-sectional enlargement, the surgical object can be held more stably by the support. Since the surgical object is held in an area of its shank in which its cross section is greater anyway, the possible contact surfaces chosen between the holding means and the surgical object can be quite large, which improves the stability. In addition, the hold in the area of the cross-sectional enlargement has the effect that a head of the surgical object, for example a screw head of a bone screw or a nail head of a bone nail, has to protrude only very slightly beyond these holding means, which reduces the overall structural height.

The holding means preferably comprise at least one holding surface, and the surgical object can be held by contact of the holding surface with the cross-sectional enlargement. Since the surgical object is thus held in an area of its shank in which its cross section is greater anyway, this holding surface can also be so great as to permit a particularly stable hold.

The support preferably comprises at least one holding projection, which has the holding surface. The holding projection can extend radially inward with respect to an axis of a receiving opening, as described below, of the support. Alternatively, it can extend parallel to this axis.

In some embodiments, the holding projection can have an in particular rounded and/or beveled insertion surface, which is designed and arranged in such a way that, when the object is inserted into the support, the holding projection is movable by means of contact of the object with the insertion surface. In particular, the holding projection can in this way be moved substantially perpendicularly with respect to an insertion direction in which the object is inserted into the support. This permits simple insertion of the object into the support, since the holding projection automatically moves during insertion into a position in which it does not impede the insertion. In addition, a rounding or beveling of the holding projection can avoid damage to a thread on a screw shank, which damage could otherwise occur during insertion of the bone screw.

Advantageously, the at least one holding surface is arranged in such a way that the cross-sectional enlargement of a surgical object received by the support can be held by a force that acts on the cross-sectional enlargement in the radial direction. This radial holding force can in particular be a clamping force. In this way, the surgical object is held in a particularly stable manner. Alternatively, the surgical object can also just be braced by the holding means, as a result of which a tilting of the screw axis can be prevented.

In a number of possible embodiments, the holding means can have at least two holding surfaces, which are in particular at a distance from each other and which are arranged in such a way that they enclose the cross-sectional enlargement of a surgical object received by the support. This further reduces the risk of tilting of a longitudinal axis of the surgical object. The longitudinal axis can be defined, for example, by the screw axis of a bone screw. If the holding surfaces are at a distance from each other, this means that at least part of the cross-sectional enlargement can remain contact-free. This facilitates the matching fit between the holding means and the cross-sectional enlargement. In addition, this means that a larger part of the surface of the surgical object is accessible for cleaning and sterilization.

The holding surfaces preferably cover 0.1% to 100%, more preferably 5% to 50%, particularly preferably 15% to 25% of the circumference of the cross-sectional enlargement of the bone screw.

Advantageously, the holding means alternatively or additionally comprise a supporting surface by means of which an underside of the cross-sectional enlargement of the surgical object can be braced. The underside of the cross-sectional enlargement of a bone screw signifies that side of the cross-sectional enlargement directed away from the screw head. Correspondingly, the underside of the cross-sectional enlargement of a bone nail signifies that side of the cross-sectional enlargement directed away from the nail head.

The invention additionally relates to a unit composed of a support, as described above, and of at least one elongate surgical object that has a shank and, arranged on the shank, a cross-sectional enlargement. The surgical object can be, for example, a bone screw or a bone nail. According to the invention, the cross-sectional enlargement is held, in particular clamped, by the holding means of the support.

A further aspect of the invention concerns a support for receiving at least one surgical object in a receiving position. The support can have one, several or all of the features described above. The object can be, for example, a bone screw, a bone pin, a bone nail, a bone plate or a disposable surgical instrument, such as a disposable drill. The bone screw or bone nail can also have one, several or all of the features described above. For example, it can be a bone screw or a bone nail with a cross-sectional enlargement. The support comprises a main body, and a supporting surface, which is designed and arranged in such a way that a supporting area of the object can be brought into contact with the supporting surface in the receiving position. The object can be removed from the receiving position in a removal direction. The removal direction extends at an angle of at most 45° to, preferably at an angle of at most 20° to, and particularly preferably substantially parallel to, a longitudinal axis of the object received in the receiving position.

According to the invention, the support has at least one holding surface, which is movable relative to the main body and which is designed and arranged in such a way that the object can be held in the receiving position by means of the holding surface.

The object can be held in particular with a force fit, for example clamped. Alternatively or in addition, it is also possible for the object to be held with a form fit. For example, the holding surface can engage in the space between two thread turns of a bone screw. A movement of the bone screw in the longitudinal direction thereof can be limited in this way.

The support can have at least two holding surfaces, which are movable relative to the main body and between which the object can be held, in particular clamped.

Alternatively or in addition, the support can have a holding surface which is movable relative to the main body and comprises at least two holding surface portions between which the object can be held, in particular clamped. It is within the scope of the invention that the holding surface is a continuous surface and the holding surface portions are not separated from one another by any structural configurations, for example grooves. The holding surface portions can therefore be purely imaginary separate portions of one and the same surface.

In the context of the present invention, the supporting surface is also understood as an edge, i.e. a one-dimensional surface area. However, the supporting surface is preferably a two-dimensional surface area.

In the context of the present invention too, the holding surface is also understood as an edge, i.e. a one-dimensional surface area. However, in this case too, it is preferably a two-dimensional surface area.

By virtue of the holding surface according to the invention, it is possible to hold a surgical object securely in the support. Since additional covers such as the one disclosed in WO 2005/092231 are therefore superfluous, the overall size of the structure is smaller.

A plurality of the supports, with surgical objects received therein, can be arranged next to one another, for example on a base plate of a surgical container. Particularly in the case of elongate objects, for example bone screws or bone nails, it is expedient, in order to save space, to arrange the supports in such a way that the longitudinal axes of the objects are oriented approximately perpendicularly with respect to the base plate. Because of the angle between the removal direction and the longitudinal axis, the objects can then be removed at an angle of at most 45° to, preferably at an angle of at most 20° to, a perpendicular to the base plate, or particularly preferably even substantially parallel to the base plate. The individual supports do not therefore have to be taken individually out of the container before the object can be removed, as is the case, for example, in the support disclosed in WO 01/49198.

When the surgical object is received, the supporting surface of the support is in contact with a supporting area of the object. The supporting surface thus defines the intended receiving position of the surgical object relative to the support. The object is particularly well supported by the supporting surface if this involves a two-dimensional surface area, i.e. not just a one-dimensional edge. The surgical object is held in this receiving position by means of the holding surface or holding surface portions. The object is held particularly well by the holding surface or the holding surface portions if these involve two-dimensional surface areas, i.e. not just one-dimensional edges. Of course, it is also conceivable, and within the scope of the invention, that the supporting surface not only supports the object but additionally clamps it.

Since the holding surface is movable relative to the main body, this provides two surfaces separate from each other. In particular, the holding surface and the supporting surface can be spatially separate from each other. Therefore, the object is also held, in particular clamped or supported, in two areas at a distance from each other, which can lead to particularly stable storage.

In some embodiments, the holding surface of the support is designed and arranged in such a way that the object, in the receiving position, can be held by means of the holding surface in a holding area that is arranged in the area of a shank of the object. In particular, the object can be clamped in the holding area. The object can be, for example, a bone screw or a bone nail. The object, in particular the bone screw or the bone nail, can be held particularly securely, in particular clamped, in this holding area.

In some embodiments, the supporting surface of the support is designed and arranged in such a way that, in the receiving position, it can be brought into contact with the underside of a cross-sectional enlargement of the object. The underside forms the supporting area of the object. The cross-sectional enlargement can be, in particular, perpendicular to the longitudinal axis of the object. The cross-sectional enlargement can be, for example, the head of a bone screw or of a bone nail. The object, in particular the bone screw or the bone nail, can be particularly well supported in this supporting area. Alternatively, in the case of a bone screw having two threaded portions with different diameters, the cross-sectional enlargement can also be formed, for example, by the threaded portion of greater diameter.

The supporting surface and the holding surface are preferably at a distance from each other in the removal direction. In this way, the object can be held in a particularly stable manner and can be easily removed.

The object in the receiving position can also preferably be clamped by means of the holding surface in a clamping direction, which is substantially non-parallel to the removal direction. The clamping direction can in particular be substantially perpendicular to the removal direction. The removal of the object is made easier in this way.

Particularly preferably, the support has at least two holding surfaces, preferably at least three holding surfaces, particularly preferably exactly three holding surfaces. Moreover, the holding surfaces are preferably arranged substantially uniformly around the longitudinal axis of the object received in the receiving position. In the example where there are exactly three holding surfaces, these holding surfaces can thus be arranged at an angle of 120° in the circumferential direction around the longitudinal axis. This guarantees particularly secure and simple holding and, in particular clamping, of the object.

In preferred embodiments, the holding surface is pretensioned by spring means. A clamping action, for example, can then be effected by these spring means. Alternatively, it is also conceivable that the spring means keep the holding surface in a position, relative to the object, in which the holding surface ensures a form fit, for example by engaging in the space between two thread turns of a bone screw. Particularly preferably, the spring means comprise at least one tongue, of which the end comprises or forms the holding surface. In particular, the support can comprise several tongues, for example three tongues, each of which comprises or forms a holding surface at the end thereof.

Particularly preferably, in the receiving position, at least the end of the tongue extends in a tongue direction, which forms an acute angle with the removal direction. In particular, this tongue direction can substantially coincide with the removal direction. This permits a simple design and can make it difficult or even completely impossible to fit the object back into the support (see below).

In one possible embodiment, the tongue is connected in one piece to the main body. In particular, the entire support can be formed in one piece.

In another preferred embodiment, the support contains an insert, which comprises a spring ring and at least one of the tongues, preferably all of the tongues. The spring ring is arranged around the longitudinal axis of the object. It can, for example, be adhesively bonded or clamped in a receiving opening of the support, in which receiving opening the object is at least partially received. The spring ring can be closed, or it can also have a gap, which makes clamping in a corresponding groove easier. The at least one tongue extends from the spring ring.

In some embodiments, at least part of the supporting surface is likewise arranged at the end of the tongue. In other embodiments, at least part of the supporting surface, in particular the entire supporting surface, is arranged on the main body of the support and can be formed by part of the surface of the main body.

Particularly preferably, the holding surface is designed and arranged in such a way that the object, in the receiving position, is substantially immovable in a direction different than the removal direction. This ensures that the object cannot be accidentally moved into a position, relative to the main body of the support, from which it can no longer be removed.

Particularly preferably, the holding surface is designed and arranged in such a way that the object is movable in the removal direction by application of a first force, and, in a second direction different than the removal direction, is substantially immovable or is movable only by application of a second force that is greater than the first force. The second direction can in particular be the direction counter to the removal direction. By virtue of this function, the object can be removed from the support by application of a certain force but can only be reinserted into the support with a greater force, if indeed it can be reinserted at all. This effect can be achieved by the holding surfaces being arranged at the ends of tongues, which ends are oriented substantially in the removal direction.

Particularly preferably, the holding surface can be brought, in particular by the spring means, into a blocking position in which the object can no longer be received in the support. This ensures that an object, once it has been removed, cannot be reinserted into the support. An object that has been accidentally removed, and that has possibly become nonsterile, can therefore only be reinserted into the support with difficulty and cannot give the false impression of being sterile.

In some embodiments, the support also has connecting means by which it can be connected to a storage unit. The connecting means can be guide projections, for example. The storage unit can, for example, comprise two guide rails of a surgical container.

The main body of the support can, for example, comprise or consist of a biocompatible plastic, such as PPSU or PEEK. It can be produced by injection molding, for example, or by milling. Alternatively, it can comprise or consist of an in particular biocompatible metal or nonmetal.

In the longitudinal axis, the main body can have a height of 5 mm to 100 mm, preferably of 5 mm to 30 mm, particularly preferably of 5 mm to 15 mm. Perpendicular to the longitudinal axis, it has a length and a width. The length can be in the range of 3 mm to 25 mm. In some embodiments, the length can preferably be in the range of 10 mm to 22 mm, particularly preferably in the range of 15 mm to 20 mm. In other illustrative embodiments, the length can be in the range of 5 mm to 20 mm, particularly preferably of 8 mm to 15 mm. The width can be in the range of 3 mm to 25 mm, preferably of 4 mm to 15 mm, more preferably of 5 mm to 15 mm, particularly preferably of 5 mm to 10 mm, and very particularly preferably of between 6 mm and 10 mm. The main body is preferably substantially cuboid.

The insert can, for example, comprise or consist of a biocompatible metal that is suitable for surgical applications, such as titanium, a stainless spring steel or a metal alloy. The insert can be produced, for example, by punching, etching or laser-cutting and subsequent bending. Alternatively, it can comprise or consist of an in particular biocompatible plastic and can be produced, for example, by milling or injection molding.

A further aspect of the invention concerns an osteosynthesis set comprising at least one support for receiving at least one surgical object, at least one surgical object held by the support in a receiving position, and at least one removal tool for removing the surgical object from the support in a removal direction. The surgical object can be in particular a support of the kind described above. The surgical object, in the receiving position, is held by the support with a first holding force.

According to the invention, the removal tool, by being moved in a direction counter to the removal direction, can be brought into contact with the surgical object in such a way that, in the receiving position, a second holding force acts between the removal tool and the surgical object, which second holding force is greater than the first holding force.

Because of the resulting force, the surgical object can be removed from the support in the removal direction. Thus, the movement of the removal tool in the removal direction is on its own sufficient to generate this required resulting force. The surgical object can therefore be removed particularly easily from the support.

The first holding force is preferably a first clamping force. The surgical object can be held particularly securely by the support by means of a clamping force. Moreover, means for generating a clamping force impose only minimal requirements on the accuracy of fit.

In preferred embodiments, the support has at least one holding surface, which is in contact with the surgical object in the receiving position. This contact effects the first clamping force. The support can have a holding projection, which is of the kind described above and comprises the holding surface.

The second holding force is likewise preferably a second clamping force. The removal tool itself is particularly advantageously designed for the intended handling of the surgical object. The surgical object can therefore be used directly with the removal tool, for example during an operation.

In some embodiments, the surgical object is a bone screw and the removal tool is a screwdriver. The second holding force, in particular the second clamping force, can act, for example, between the blade of the screwdriver and a head of the bone screw. The blade of the screwdriver therefore simply has to be fitted into an opening in the head of the bone screw. The opening in the head can be, for example, a slit, a cross recess, a Torx, a hexagon socket or a polygon. The opening can also be designed, for example, as described in DE 10 2004 026 769 or in EP 1 987 792.

The invention further relates to a unit composed of a support, as described above, and of at least one surgical object, in particular at least one bone screw and/or one bone nail. The supporting area of the object is in contact or at least can be brought into contact with the supporting surface of the support. Moreover, the object is held, in particular clamped, by means of the at least one holding surface. The support and/or the surgical object can have one, several or all of the properties described above and in particular can be arranged in a relative position to one another as is described above.

In some embodiments, the surgical object can be a bone screw, which has a shank and a cross-sectional enlargement arranged on the shank. For example, it can be an intermaxillary fixation screw. The bone screw can be held, in the area of the cross-sectional enlargement of its shank, by holding means of the support.

The invention also relates to further elements for the storage and presentation of surgical materials, in particular of bone plates for bone surgery. Conventional containers provided for this purpose, for example as disclosed in U.S. Pat. No. 5,732,821, have recesses which are adapted to the shapes of the bone plates and in which one or more bone plates can be placed. A disadvantage of these is that the surgeon is tied to the choice of bone plates defined by the recesses. The container cannot therefore be equipped on an individual basis. Moreover, gripping a bone plate is made difficult if the latter is engaged deep in the recess. In addition, effective cleaning and sterilization is difficult, especially of those bone plates located in the lower area of the recess. Finally, it is not possible to tell directly how many bone plates are still located in a recess, and this makes re-ordering considerably difficult.

These and other problems were described in the international patent application PCT/EP2007/058725 by the applicant. The latter document discloses a mounting for fixing at least one bone plate support for a bone plate on a base plate. The mounting comprises a pin, which is oriented substantially perpendicularly with respect to a base plane of the mounting. One or more bone plate supports, each with a bone plate, can be fitted onto this pin and stacked. For this purpose, the bone plate supports each have an opening.

A disadvantage of this mounting is that the bone plate supports can slip off the pin if the container, on the base plate of which the mounting is secured, is accidentally tilted.

It is a further object of the present invention to make available a mounting for fixing at least one surgical object on a base plate, which mounting overcomes these disadvantages. In particular, a surgical object fitted onto the pin should not be able to accidentally slip off.

This object is achieved by a mounting for fixing at least one surgical object, in particular a bone plate support for a bone plate, on a base plate, wherein the mounting comprises a pin. The base plate can be part of a surgical container, for example. The pin is oriented substantially perpendicularly with respect to a base plane of the mounting. The base plane is an imaginary plane that can coincide, for example, with the plane of a base plate on which the mounting is fixed according to the invention.

The surgical object can be, in particular, a bone plate support for a bone plate. However, it is also conceivable, and lies within the scope of the invention, that the surgical object is a surgical instrument, for example a bone drill, or auxiliaries.

Along section planes lying perpendicularly with respect to the longitudinal direction of the pin, the pin is substantially non-circular. Along these section planes, the pin is preferably substantially rectangular. A plurality of surgical objects, in particular bone plate supports, can be fitted onto such a pin and in particular stacked, as is described in more detail below. Since the pin is substantially non-circular along said section planes, the surgical objects can be fitted only in specific, predefined orientations relative to the pin and therefore to a base plate. This arrangement secures the objects against rotation, in order to avoid accidental turning.

According to the invention, the pin has fixing means, with the aid of which a surgical object, in particular a bone plate support, can be fixed releasably in at least one fixing position, in particular in at least two different fixing positions, along a longitudinal direction of the pin. In this way, it is possible to ensure that the object does not accidentally slip along the longitudinal direction of the pin and to ensure in particular that the object does not slip completely off the pin.

According to preferred embodiments, the fixing means comprise at least one cross-sectional narrowing and/or cross-sectional widening in a section plane lying perpendicularly with respect to the longitudinal direction of the pin. The cross-sectional narrowing can be a locking recess, for example. The cross-sectional widening can be a locking projection, for example.

The pin can, for example, comprise or consist of a biocompatible metal that is suitable for surgical applications, such as titanium, stainless steel or a metal alloy. It can be produced, for example, by milling, turning, drilling or casting. Alternatively, the pin can comprise or consist of a plastic that is suitable for surgical applications. It can be produced, for example, by milling or injection molding.

Along its longitudinal direction, the pin can have a height in the range of 5 mm to 150 mm, preferably of 10 mm to 150 mm, more preferably of 10 mm to 50 mm, still more preferably of 13 mm to 50 mm, particularly preferably of 13 mm to 30 mm, very particularly preferably of 15 mm to 20 mm. Perpendicular thereto it has a width and a thickness. The width can be in the range of 2 mm to 10 mm, preferably of 3 mm to 8 mm, particularly preferably of 3 mm to 5 mm. The thickness can likewise be in the range of 2 mm to 10 mm, preferably of 3 mm to 8 mm, particularly preferably of 3 mm to 5 mm.

The pin can have means for fixing to a base plate of a surgical container. These means for fixing can be designed, for example, as a bore that extends along the longitudinal direction of the pin. This bore can have an internal thread, which can engage with a fixing screw. In this way, the pin can be placed from above onto an apertured base plate and fixed with the fixing screw, by means of the latter being guided from underneath through an opening in the base plate and being screwed into the internal thread of the bore.

The mounting also preferably has a planar shape element, which lies in the base plane or parallel thereto and which substantially reproduces the shape of a bone plate. The planar shape element is preferably designed and arranged in such a way that, in the fixing according to the invention on a base plate, it comes into contact with the base plate. The reproduction of the shape of the base plate permits immediate identification of the shape of the bone plate provided for this mounting. It is also possible, if necessary, to equip the base plate of a surgical container with a selection of different mountings according to the invention.

Alternatively or in addition to the planar shape element, the mounting can have a marking element. The marking element lies in the base plane or parallel thereto.

In some embodiments, the marking element is or can be connected releasably to the pin. For example, the marking element can be connected releasably to the pin by clamping.

The invention further relates to a system with at least one mounting as described above, and with at least one unit that comprises a support for a surgical object and also a surgical object. For example, the unit can comprise a bone plate support and at least one bone plate. Alternatively, the unit can also comprise a support and a surgical object, for example a bone screw or a bone nail, in particular a support as described above and a bone screw. At least one support, in particular a bone plate support, has an opening passing right through it, by means of which the support is or can be fixed releasably on the pin of the mounting.

The bone plate support preferably comprises at least one clamping element, which delimits the opening extending right through the bone plate support. By means of this clamping element, the bone plate support is or can be fixed releasably on the pin of the mounting. The clamping element can be a clamping tongue, for example.

At least one bone plate support preferably has a substantially plane upper face and a substantially plane lower face arranged substantially parallel to the upper face. In this way, a flat configuration is achieved, which can ensure a high packing density. Particularly preferably, the opening extends right through the bone plate support in a direction perpendicular to the upper face and to the lower face.

It is likewise particularly preferable that at least one bone plate support has an upper holding tongue and a lower holding tongue, between which a bone plate can be clamped or is clamped.

In preferred embodiments, the upper holding tongue has at least one abutment for positioning the bone plate. The abutment can in particular extend substantially perpendicularly with respect to the upper face of the bone plate support and can have an abutment surface extending perpendicularly with respect to the upper face of the bone plate support.

Alternatively or in addition, the lower holding tongue can have at least one holding projection for holding the bone plate, in particular for clamping the bone plate. The holding projection can extend in particular substantially perpendicularly with respect to the lower face of the bone plate support.

With an abutment and/or a holding projection of this kind, a bone plate can be held, in particular clamped, only via relatively small contact points. This simplifies the delivery of a cleaning and sterilizing medium to the bone plates held by the bone plate support. The cleaning and sterilizing medium can be gaseous or liquid.

The lower holding tongue preferably has at least one irrigation opening extending right through it for the passage of a flushing medium, in particular a sterilizing medium. This makes cleaning and sterilization of the bone plate even easier.

The bone plate support can, for example, comprise or consist of a biocompatible plastic, such as PPSU or PEEK. It can be produced by injection molding, for example, or by milling. Alternatively, the bone plate support can also comprise or consist of a metal suitable for surgical applications.

The bone plate support, in particular in the direction of the holding tongues, can have a length in the range of 10 mm to 30 mm, preferably of 12 mm to 20 mm, particularly preferably of 14 mm to 18 mm. Moreover, in particular perpendicular to its upper face and to its lower face, it can have a height in the range of 2 mm to 20 mm. In some embodiments, it can have a height in the range of 2 mm to 10 mm, more preferably of 3 mm to 8 mm, particularly preferably of 4 mm to 6 mm. In other embodiments, it can have a height in the range of 3 mm to 12 mm, particularly preferably of 4 mm to 8 mm. Perpendicular to the length and to the height, it can have a width in the range of 5 mm to 30 mm, preferably of 6 mm to 20 mm, particularly preferably of 7 mm to 10 mm.

Finally, the invention also relates to a bone plate support, which in particular can be part of the systems described above. According to the invention, the bone plate support has a substantially plane upper face and a substantially plane lower face arranged substantially parallel to the upper face. In this way, a flat configuration is achieved, which can ensure a high packing density.

The bone plate support can have one, several or all of the features described above. In a preferred embodiment, the bone plate support can, for example, have an upper holding tongue and a lower holding tongue, between which a bone plate can be clamped or is clamped. Alternatively or in addition, it can have an opening extending right through it.

Finally, the invention relates to a surgical container having at least one of the elements listed below:
- at least one support, as described above, for receiving at least one surgical object;
- at least one osteosynthesis set as described above;
- at least one unit as described above;
- at least one mounting as described above;
- at least one system as described above;
- at least one bone plate support as described above.

The invention is explained in more detail below on the basis of illustrative embodiments and with reference to the figures, in which:

FIG. 9a shows a side view of the support according to the invention from FIGS. 8a and 8b, with a bone screw received therein;

FIG. 9b shows a side view of the support according to the invention from FIGS. 8a, 8b and 9a, with a bone screw received therein and with the blade of a screwdriver;

FIG. 9c shows a side view of the support according to the invention from FIGS. 8a, 8b, 9a and 9b and of the bone screw removed from the support with the aid of the screwdriver;

Figure 10:
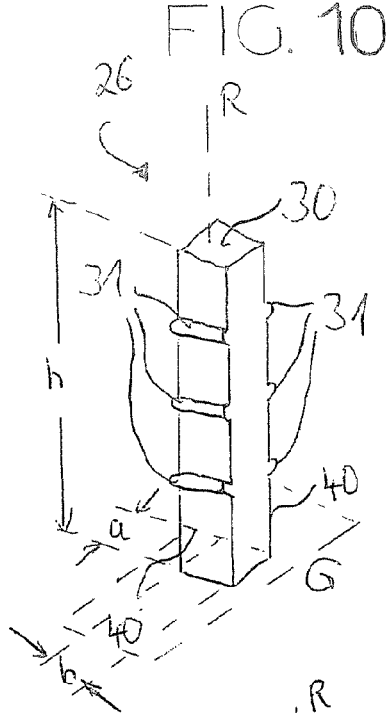
FIG. 10 shows a perspective view of a first embodiment of a mounting according to the invention for bone plate supports.
Figure 14:
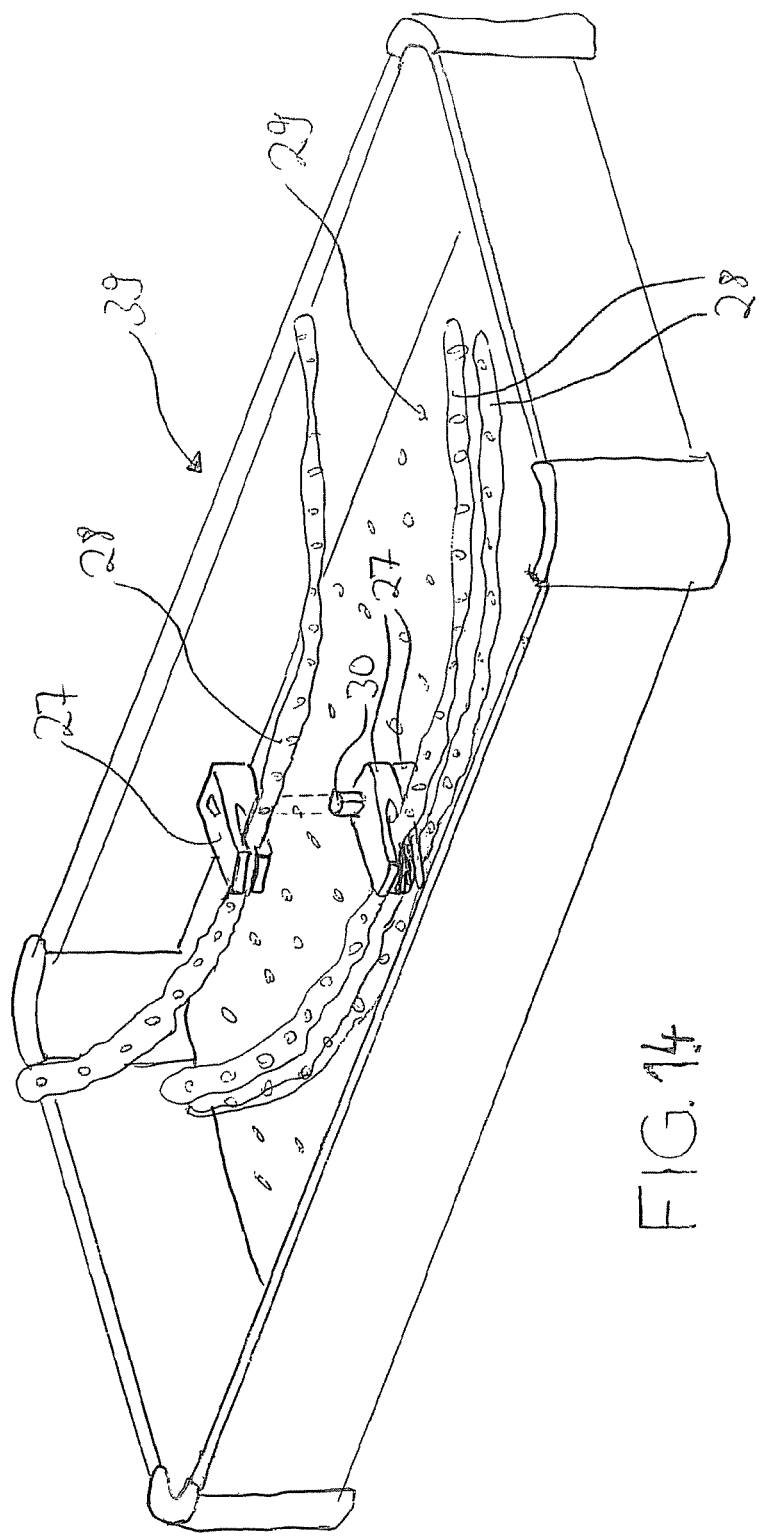
Figure 15:
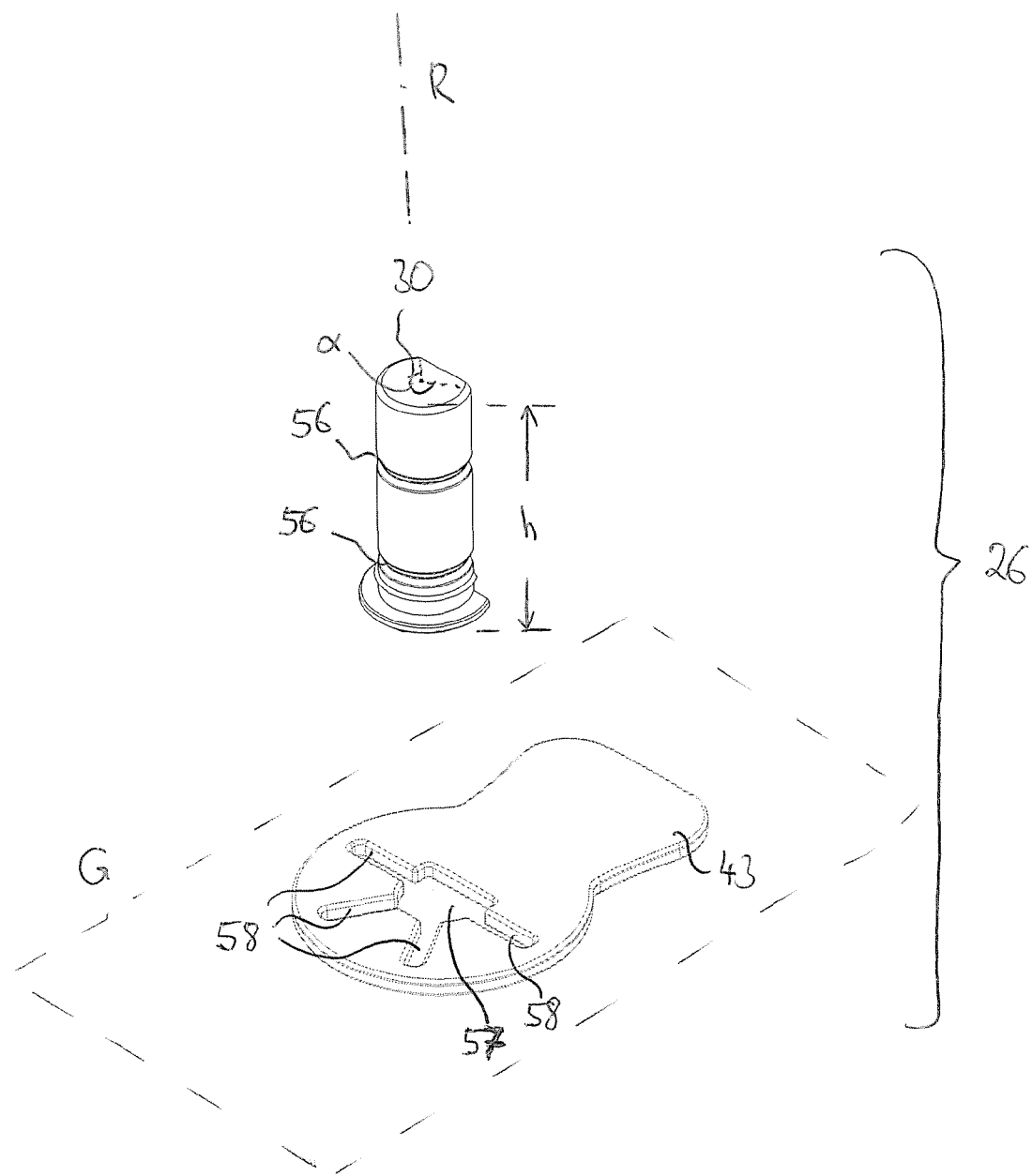
Figure 16B:
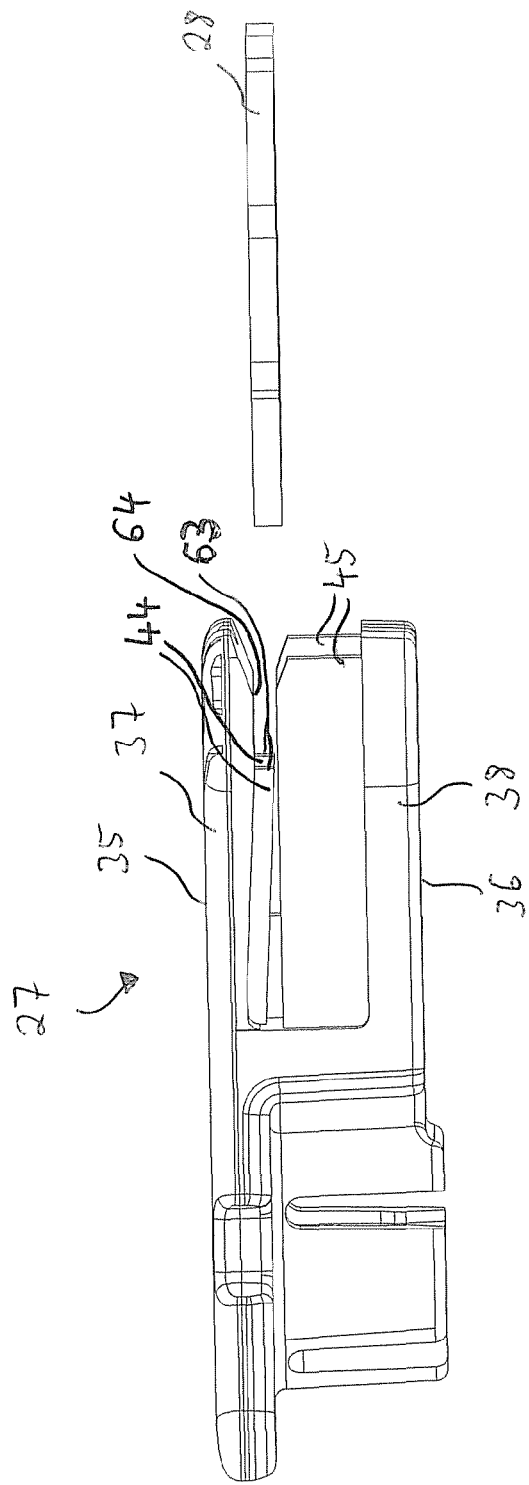
Figure 17:
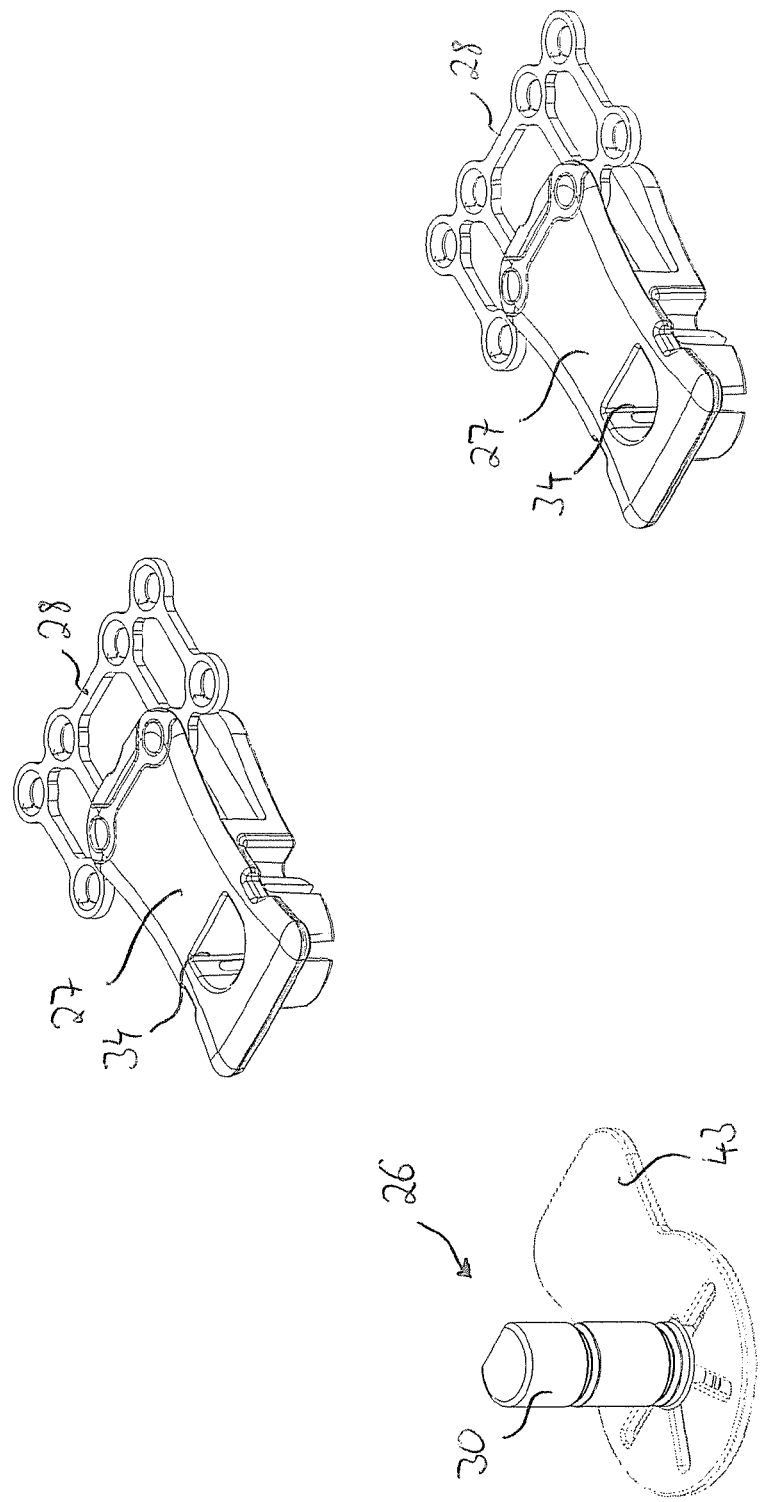
Figure 18:
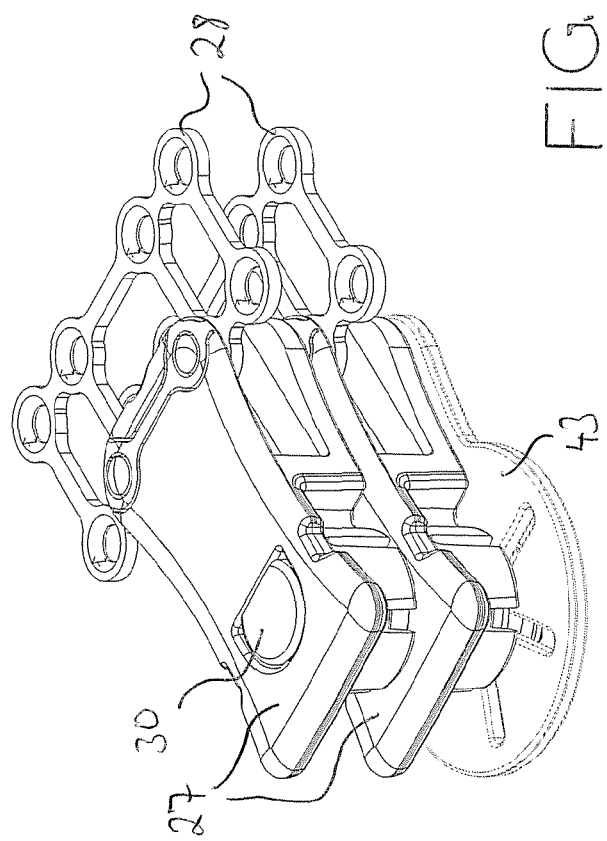
Figure 19:
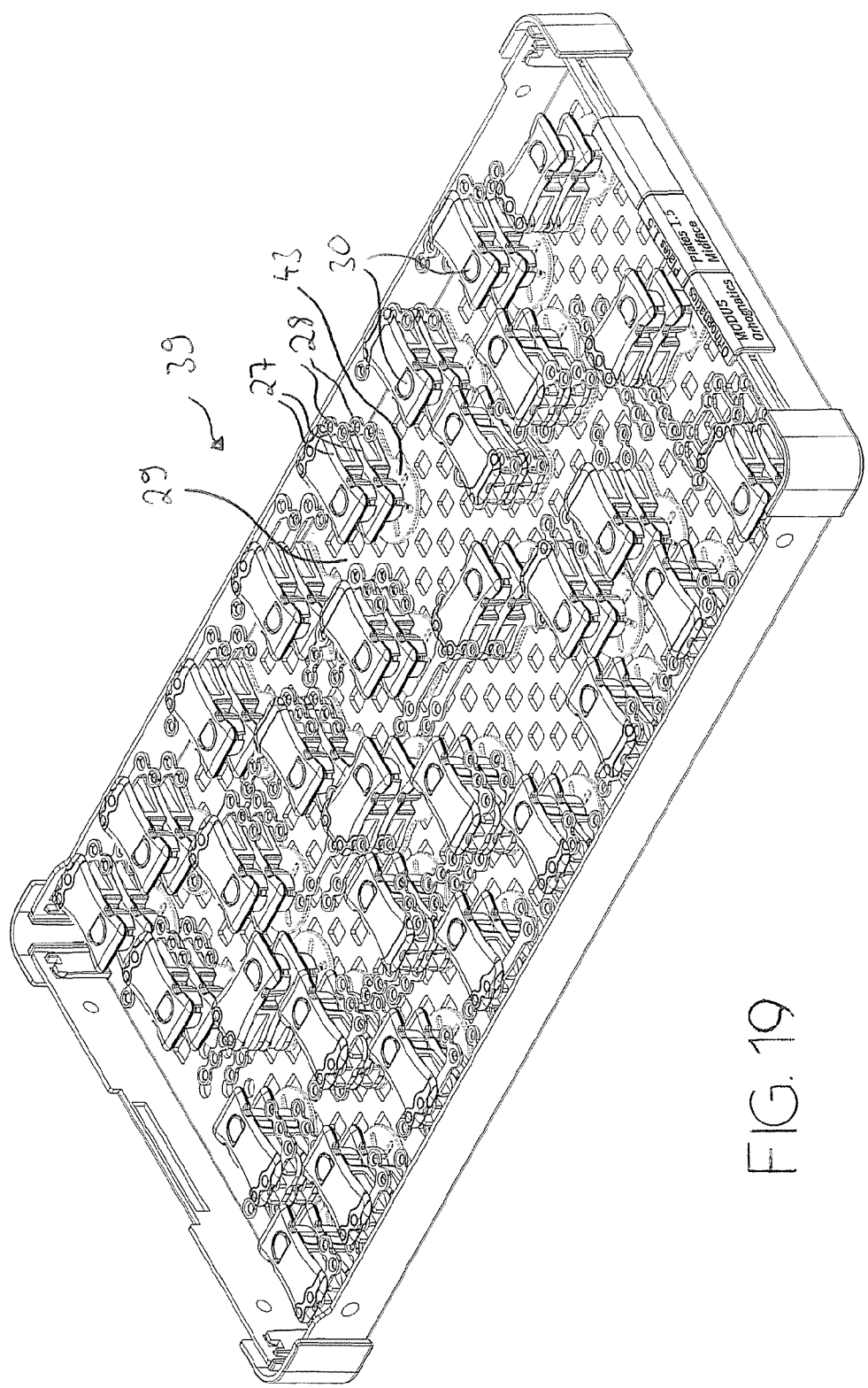
Figure 20:
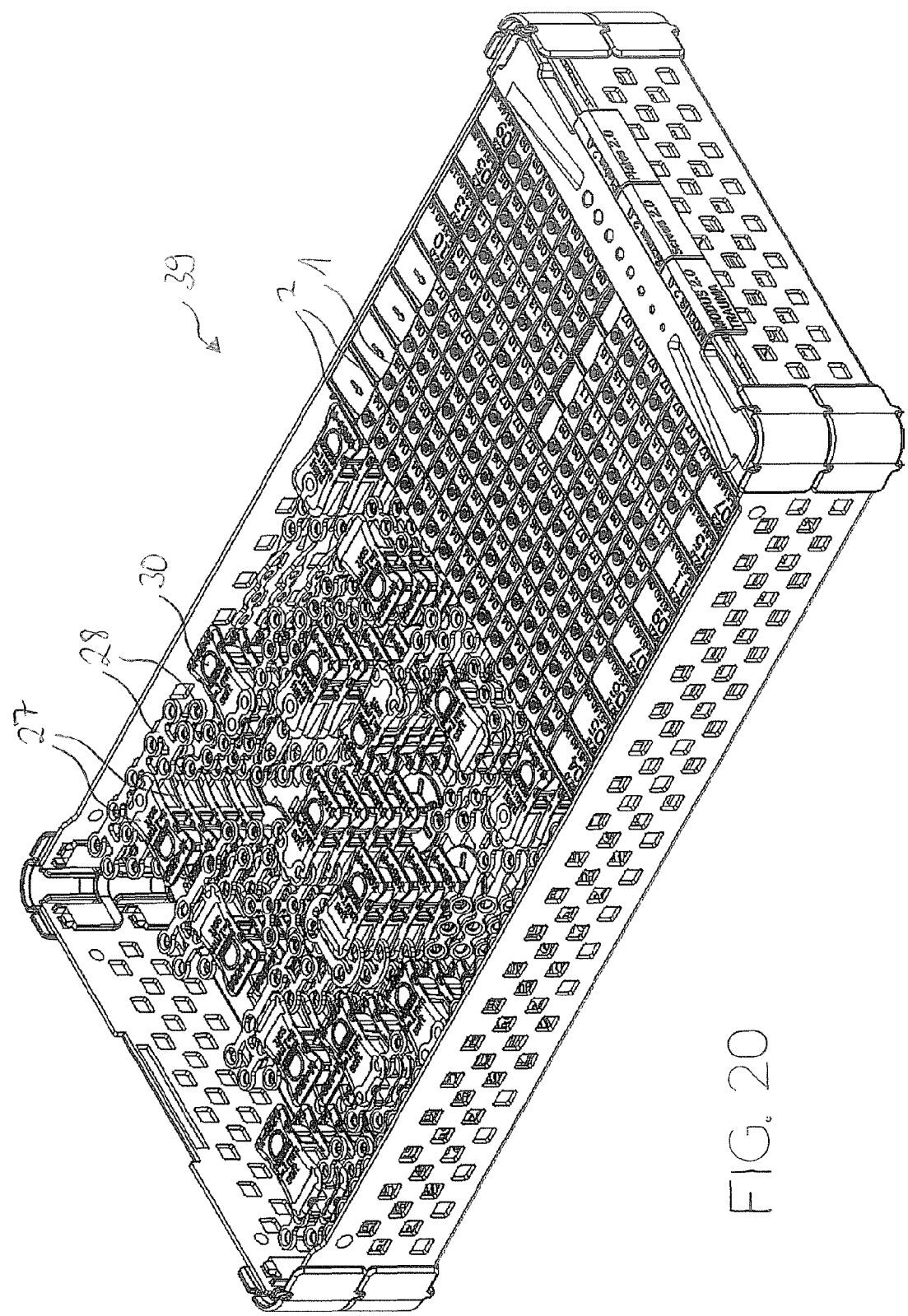

FIGS. 13a to 13d each show a plan view of a unit according to the invention composed of a bone plate support and of one of four different bone plates;

FIG. 14 shows a surgical container with a base plate, a mounting according to FIG. 10 fixed thereon, and several units stacked thereon and composed of a bone plate support and of a bone plate;

FIG. 15 shows a perspective view of a second embodiment of a mounting according to the invention;

FIGS. 16a and 16b show a perspective view from above and a side view, respectively, of a second embodiment of a bone plate support according to the invention with a bone plate;

FIG. 16c shows the bone plate support from FIGS. 16a and 16b in a perspective view from below;

FIG. 17 shows a system according to the invention, composed of the mounting according to FIG. 15 and of two bone plate supports according to FIGS. 16a to 16c, each with a bone plate;

FIG. 18 shows the system according to FIG. 17, with the bone plate supports connected to the mounting;

FIG. 19 shows a surgical container with a plurality of systems according to FIG. 18;

FIG. 20 shows another surgical container with a plurality of systems according to FIG. 18 and with a plurality of supports, each with a bone screw.

Figure 1A:
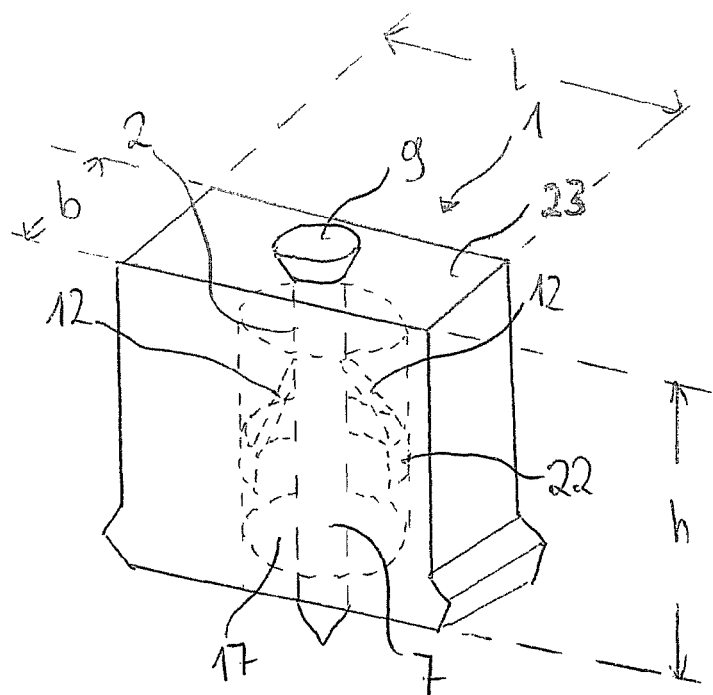
FIGS. 1a and 1b show a perspective view and a sectional side view, respectively, of a first embodiment of a support according to the invention, with a bone screw received therein.

FIG. 1a shows a perspective view of a first embodiment of a support 1 according to the invention, with a bone screw 2 received therein. The bone screw 2 forms an elongate surgical object. The support 1 comprises a main body 23, from which a head 9 of the bone screw 2 protrudes. A shank 7 of the bone screw 2 extends into a receiving opening 17 of the main body 23, where it is clamped with the aid of tongues 12, which are part of an insert 22 (see below).

Figure 1B:
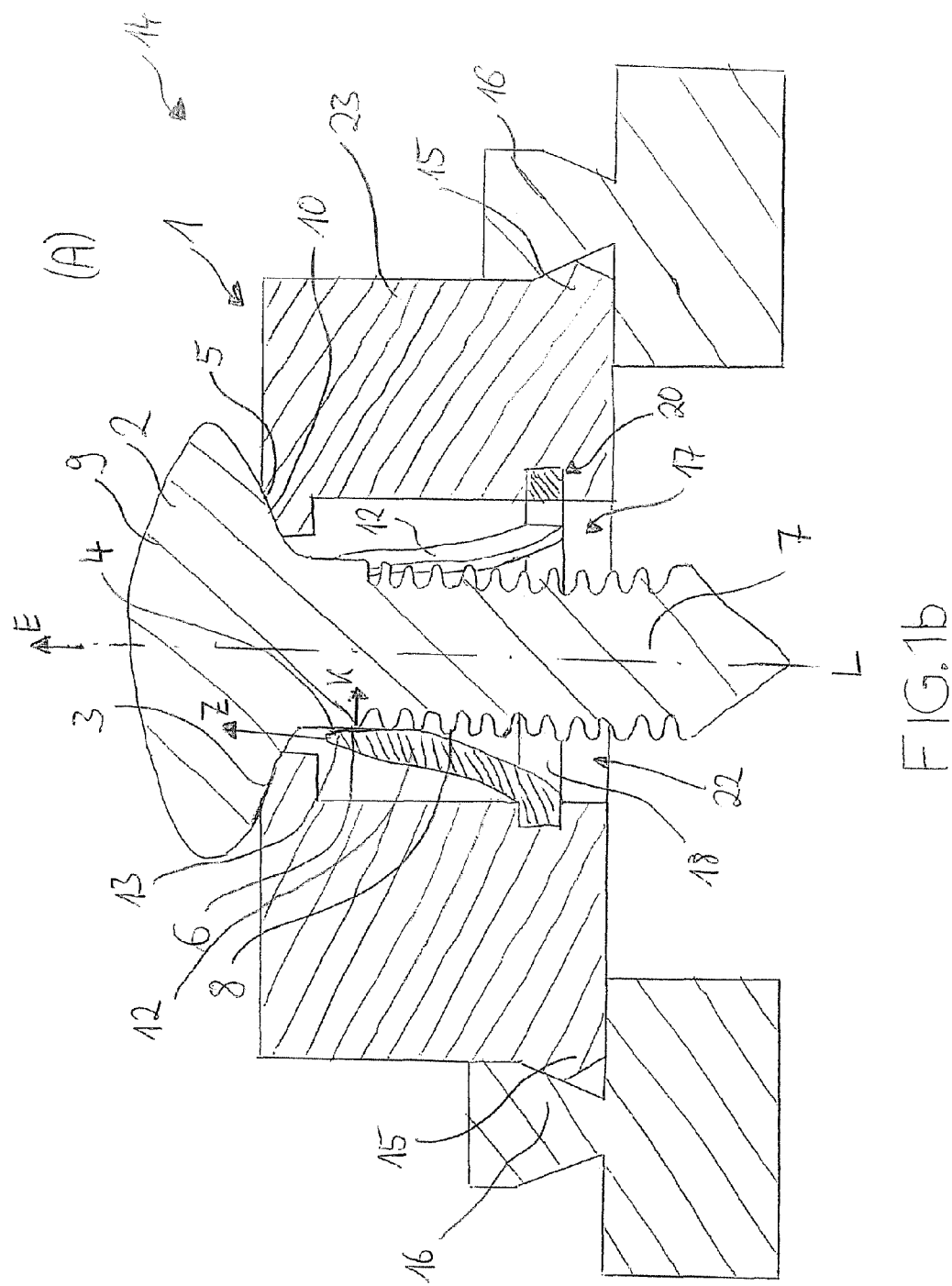

FIG. 1b shows a sectional side view of the support 1 with the bone screw 2 received therein. The head 9 of the bone screw 2 forms a cross-sectional enlargement, of which the underside 10 is in contact with a supporting surface 3 of the support 1. Part of the underside 10 of the head 9 of the bone screw 2 thus forms a supporting area 5 of the bone screw 2. The supporting surface 3 defines the receiving position A, as shown in FIG. 1b, of the bone screw 2 with respect to the support 1.

The shank 7 of the bone screw 2 protrudes into the receiving opening 17 of the support 1. A spring ring 18 of an insert 22 is clamped in a circumferential groove 20 of the main body 23 of the support 1 (cf. detail view in FIG. 2). Three tongues 12 extend from the spring ring 18. Each of the three tongues 12 has an end 13, which is movable relative to the main body 23 and which extends in a tongue direction Z and in each case comprises a holding surface 4. The supporting surface 3 and the holding surfaces 4 are at a distance from each other in the removal direction E. The bone screw is clamped between the holding surfaces 4 and is in this way held in the support 1. The holding surfaces 4 are arranged uniformly around a longitudinal axis L of the bone screw 2. In this way, the bone screw 2 is clamped in a clamping direction K in a clamp area 6. The clamp area is arranged in the area of the thread 8 of the shank 7. The clamping action is imparted by the tongues 12, which form spring means by which the holding surfaces 4 are pretensioned.

The bone screw 2 can be removed in a removal direction E by application of a first force. The support 1 and in particular the supporting surface 3 and the holding surfaces 4 are designed and arranged in such a way that the bone screw 2 is removable parallel to its longitudinal axis L. The tongue direction Z coincides substantially with the removal direction E. This has the result that the bone screw 2 is substantially immovable in a direction counter to the removal direction E or is movable only by application of a second force that is greater than the first force. The clamping direction K is perpendicular to the removal direction E.

The support 1 also has connecting means in the form of guide projections 15. With the aid of these guide projections 15, the support 1 according to FIG. 1b is connected to two guide rails 16, forming a storage unit for one or more supports 1. The support 1 is thus movable along the guide rails 16 in a direction perpendicular to the plane of the drawing.

Figure 2:
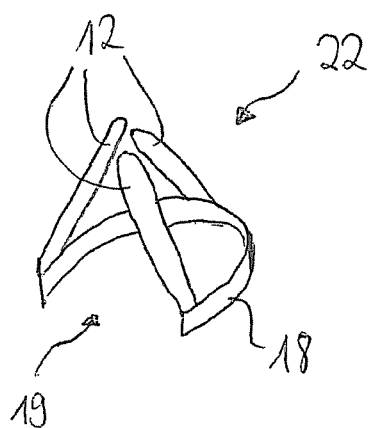
FIG. 2 shows a perspective detail view of an insert of the support according to FIGS. 1a and 1b.

FIG. 2 shows a detail view of the insert 22 of the support 1 according to FIGS. 1a and 1b. This insert 22 has a spring ring 18 with a gap 19. Three tongues 12 extend from the spring ring 18.

Figure 3:
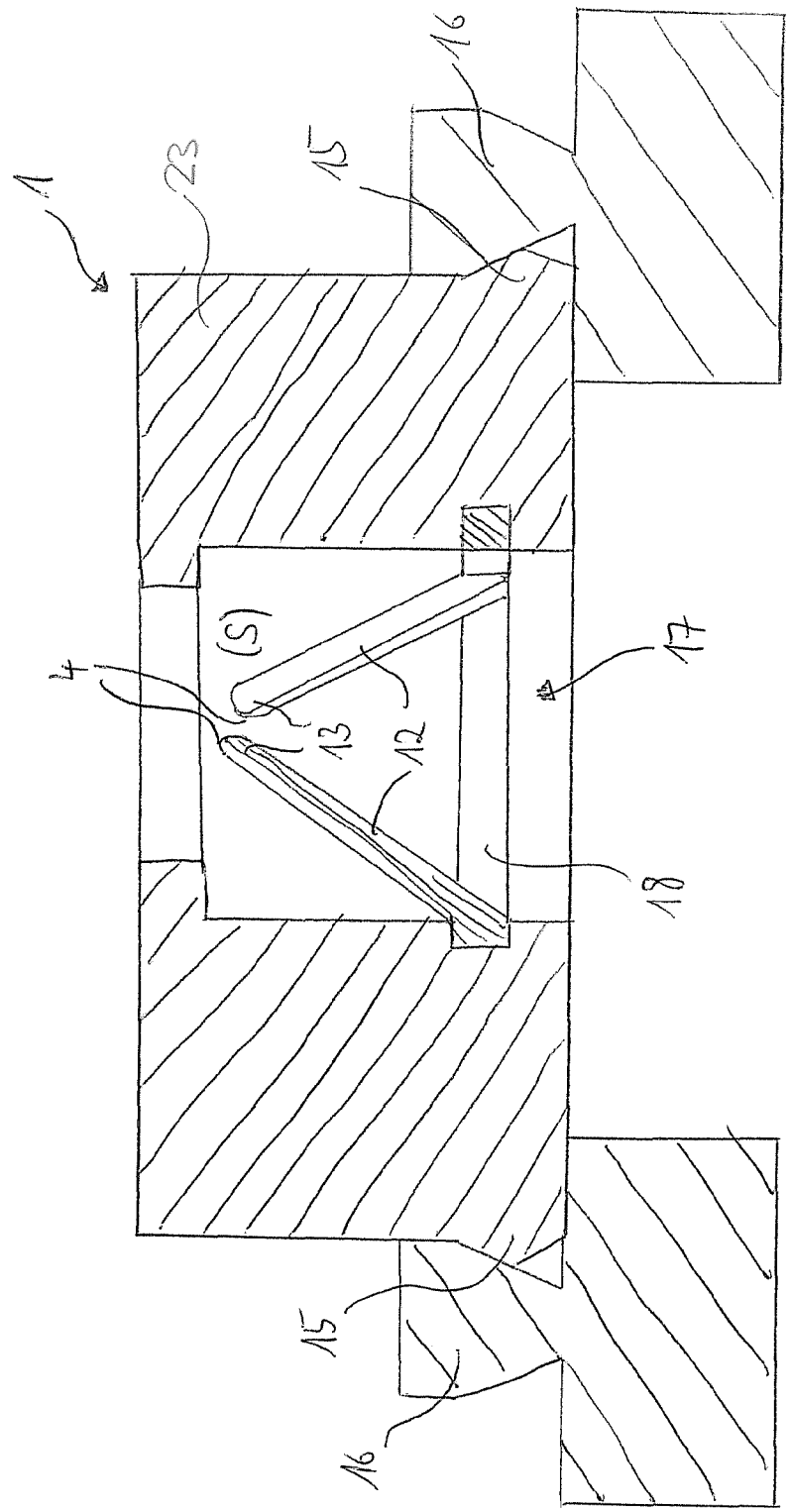
FIG. 3 shows a sectional side view of the support according to FIGS. 1a and 1b without a bone screw.

In FIG. 3, the support 1 according to FIGS. 1a and 1b is shown in a sectional side view without a bone screw. The pretensioning of the tongues 12 means that their ends 13 are forced radially further into the receiving opening 17 when the bone screw is removed. In this position of the tongues 12 and of the holding surfaces 4, the bone screw can no longer be inserted into the support 1. Within the meaning of the invention, the holding surfaces 4 are thus located in a blocking position S. As a result, a bone screw that has been accidentally removed and has possibly become non-sterile cannot be inserted again into the support 1.

The main body 23 of the support 1 can be made, for example, of a biocompatible plastic, such as PPSU or PEEK. It can be produced by injection molding, for example, or by milling. Alternatively, the main body 23 can comprise or consist of an in particular biocompatible metal. Except for the guide projections 15, the main body 23 is substantially cuboid and has a length l of 18 mm, a width b of 8 mm and a height h of 8 mm.

The insert 22 can be made, for example, of a biocompatible metal such as titanium or steel. The insert 22 can be produced, for example, by punching, etching or laser-cutting and subsequent bending. Alternatively, it can comprise or consist of an in particular biocompatible plastic and can be produced, for example, by milling or injection molding.

Figure 4:
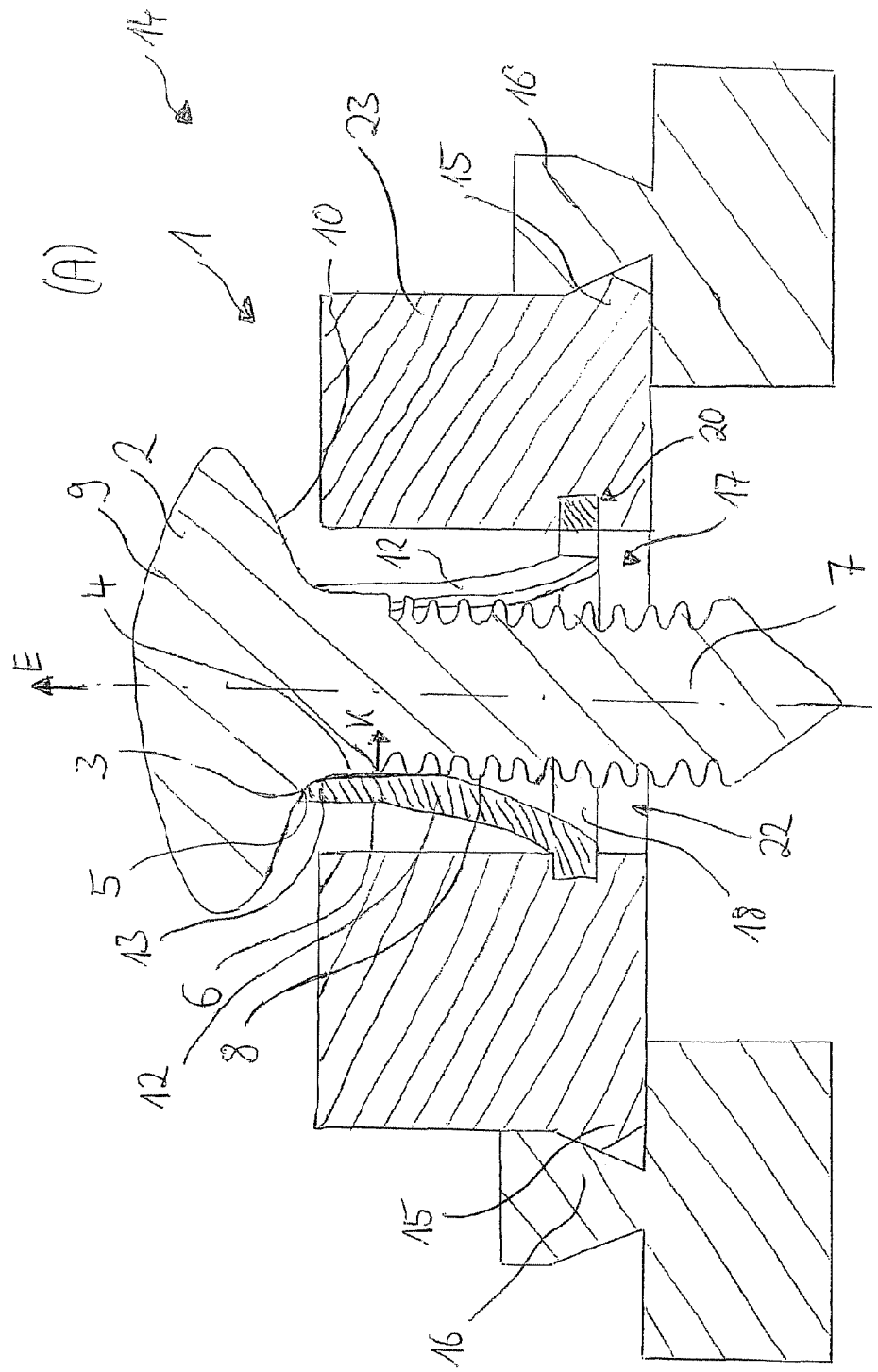
FIG. 4 shows a sectional side view of a second embodiment of the support according to the invention.

FIG. 4a shows a sectional side view of a second embodiment of the support 1 according to the invention, with a bone screw 2 received therein. In contrast to the first illustrative embodiment, the supporting surfaces 3 are not arranged here on the main body 23 of the support 1 but likewise on the ends 13 of tongues 12. In this illustrative embodiment too, the supporting surfaces 3 are in contact with an underside 10 of a head 9 of the bone screw 2. Such an embodiment can be produced more easily and at less cost.

Figure 5A:
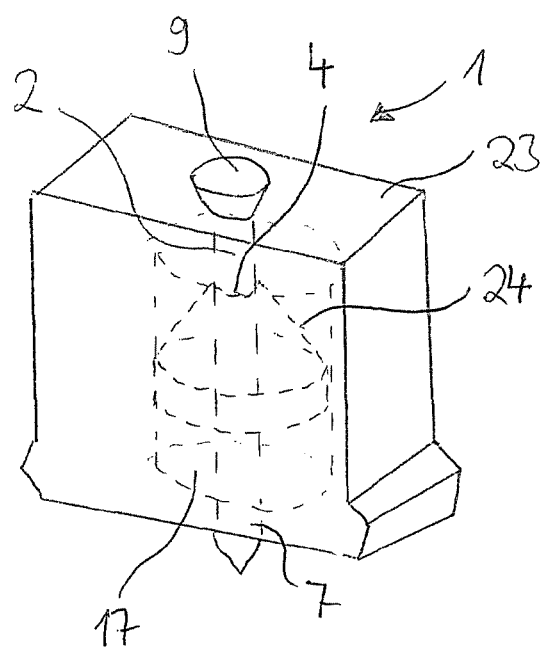
FIGS. 5a and 5b show a perspective view and a sectional side view, respectively, of a third embodiment of the support according to the invention.
Figure 5B:
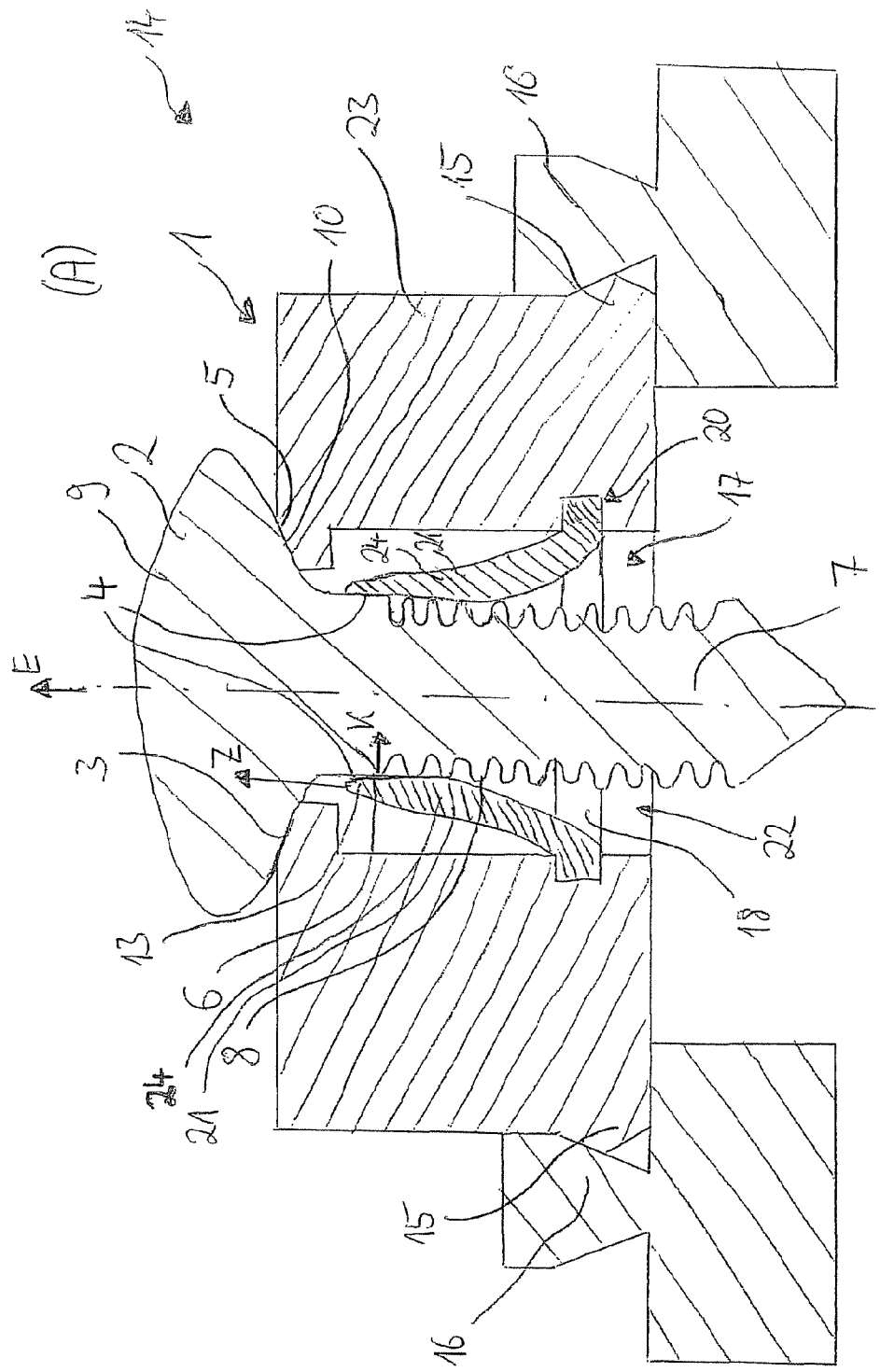

FIGS. 5a and 5b show a third illustrative embodiment of a support 1 according to the invention, with a bone screw 2 received therein. FIG. 5a shows the support 1 in a perspective view. In contrast to the first illustrative embodiment according to FIGS. 1a to 3, the support 1 does not comprise tongues, but a collar 24, of which the circular edge forms a single continuous holding surface 4. As can be seen from the sectional side view according to FIG. 5b, the shank 7 of the bone screw 2 is clamped between two holding surface portions 21 of the holding surface 4.

Figure 6A:
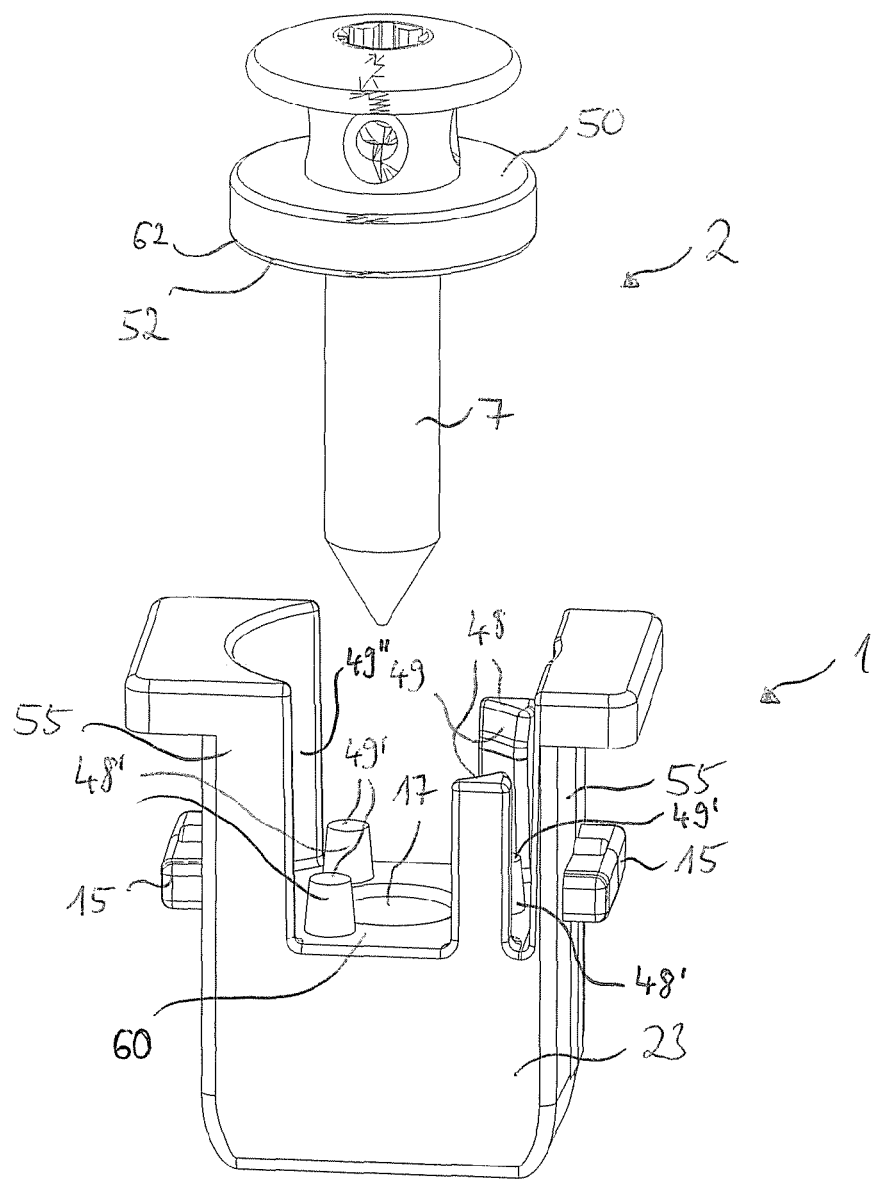
FIG. 6a shows a perspective view of a fourth embodiment of the support according to the invention.
Figure 6B:
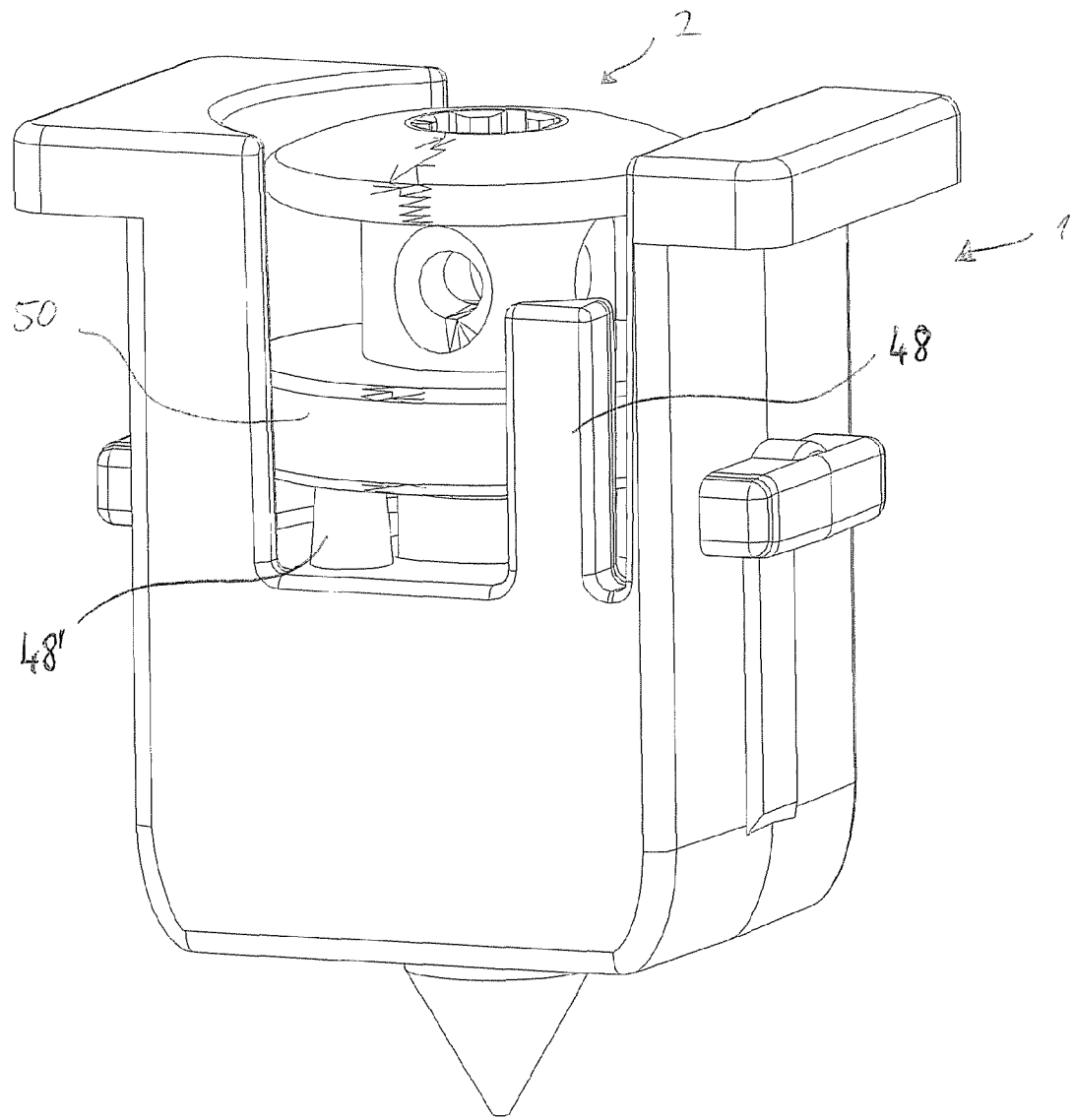
FIG. 6b shows a sectional side view of the support according to the invention from FIG. 6a, with a bone screw inserted therein.

FIGS. 6a and 6b show a fourth embodiment of the support 1 according to the invention. According to the perspective view in FIG. 6a, the support 1 has a main body 23 with two side parts 55 and a receiving opening 17 for a bone screw 2. The bone screw 2 has a shank 7, and a cross-sectional enlargement 50 arranged on the shank 7. This bone screw 2 is an intermaxillary fixation screw. The support 1 comprises connecting means in the form of guide projections 15. With the aid of these guide projections 15, the support 1 can be moved along guide rails analogously to FIG. 4.

The support 1 comprises a substantially rectangular upper face 60, which is arranged perpendicularly with respect to the receiving opening 17. The support 1 also has five holding projections 48, 48', of which four are arranged in each case at one of the four corners of the upper face 60. A further holding projection 48' is arranged between two corners of the upper face 60 and adjacent to one of the side parts 55. The holding projections 48, 48' extend perpendicularly from the upper face 60 and thus parallel to the receiving opening 17. Two of the holding projections 48 have a first length along their extent parallel to the receiving opening 17, while the three other holding projections 48' are designed as truncated cones and have a second length along their extent parallel to the receiving opening 17, which second length is shorter than the first length.

The holding projections 48, 48' each have a holding surface 49, 49' with which a bone screw 2 can be held via a cross-sectional enlargement 50 of its shank 7 (cf. FIG. 6b below). The holding surfaces 49 of the holding projections 48 with the first length are arranged in such a way that the cross-sectional enlargement 50 can be held by a holding force that acts radially on the cross-sectional enlargement 50. A further holding surface 49" is formed by a part of the surface of the side part 55, which lies opposite the holding projections 48 with the first length. This surface is slightly conical. In the case of a cross-sectional enlargement 50 with a cylindrical outer face, a linear contact is then obtained between a part of the lower edge 62 of the cross-sectional enlargement 50 and the holding surface 49". In this way, the cross-sectional enlargement 50 is clamped radially by the three holding surfaces 49, 49".

The holding surfaces 49' of the holding projections 48' with the second length are arranged in such a way that the cross-sectional enlargement 50 can be held by a holding force that acts in an axial direction on the cross-sectional enlargement 50. In this way, the cross-sectional enlargement 50 can be supported in the axial direction by a three-point bearing.

The five holding surfaces 49, 49' are arranged at a distance from one another in order to simplify the delivery of liquid or gaseous cleaning and sterilizing agent.

FIG. 6b shows another perspective view of the support 1 according to FIG. 6a, with the bone screw 2 inserted therein. The bone screw 2 is laterally clamped by virtue of the fact that the two holding surfaces 49 of the holding projections 48 with the first length are in contact with the cross-sectional enlargement 50 of the bone screw 2. In this way, a holding force is generated that acts radially on the cross-sectional enlargement 50, said holding force in this case being a clamping force. The underside 52 of the cross-sectional enlargement 50 is supported on the holding surfaces 49' (not visible here) of the holding projections 48' with the second length.

The support 1 according to FIGS. 6a and 6b has a height of 9.6 mm parallel to the axis of the receiving opening 17, a width of 5.9 mm parallel to the guide projections 15, and a depth of 9.8 mm perpendicular to both of these directions.

Figure 7A:
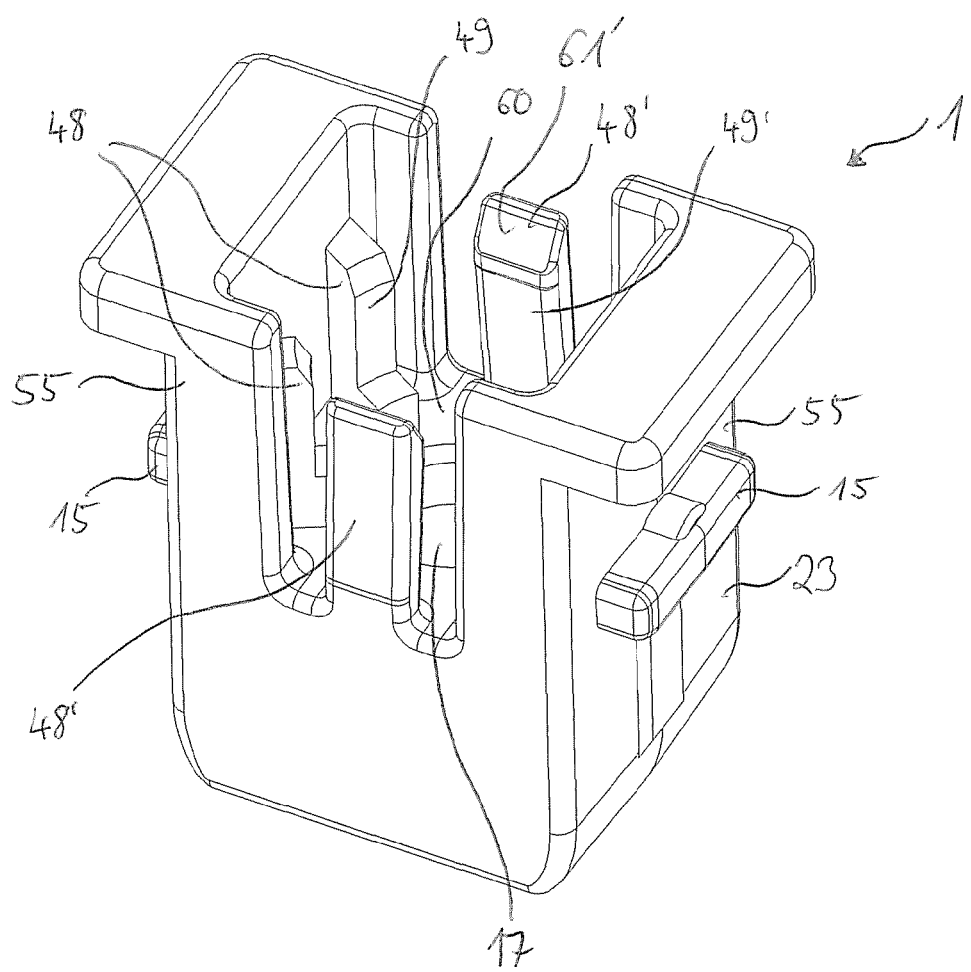
FIG. 7a shows a perspective view of a fifth embodiment of the support according to the invention.
Figure 7B:
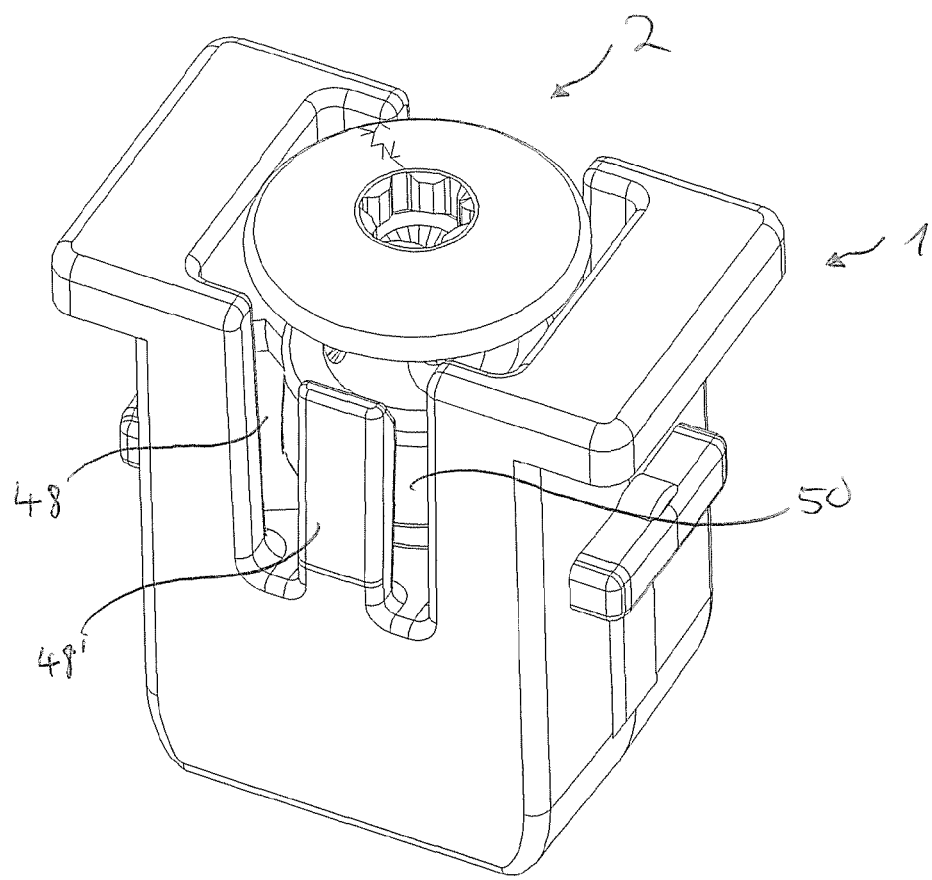
FIG. 7b shows the support according to the invention from FIG. 7a with a bone screw inserted therein.

Moreover, FIGS. 7a and 7b show a fifth illustrative embodiment of a support 1 according to the invention. This support 1 according to FIG. 7a likewise has a main body 23, two side parts 55, two guide projections 15, an upper face 60 and, extending perpendicularly with respect to the latter, a receiving opening 17 for a bone screw (not shown here). The support 1 in this illustrative embodiment has a total of six holding projections 48, 48', of which only four can be seen here. Two holding projections 48 extend respectively from each of the two side parts 55. The two other holding projections 48' extend perpendicularly from the surface 60 and therefore parallel to the receiving opening 17.

Each of the holding projections 48, 48' has a holding surface 49, 49' directed radially inward in relation to the axis defined by the receiving opening 17. These six holding surfaces 49, 49' are all at a distance from one another and can enclose the cross-sectional enlargement of a bone screw received by the support (cf. FIG. 7b below). In this way, the inserted bone screw can be held particularly securely.

At their upper end, the holding projections 48' each have a beveled insertion surface 61', and these insertion surfaces 61' are adjacent to the holding surfaces 49'. These insertion surfaces 61' are designed and arranged in such a way that, when a bone screw is inserted into the support, the holding projections 48' are movable radially outward by virtue of the object being in contact with the insertion surfaces 61'. This permits simple insertion of the bone screw 2 into the support 1, since the holding projections 48', by virtue of their flexibility, automatically move during insertion into a position in which they do not impede the insertion.

FIG. 7b shows the support 1 from FIG. 7a, with a bone screw 2 with cross-sectional enlargement 50 inserted therein. The holding surfaces (not visible here) of the holding projections 48, 48' radially hold the bone screw 2 via the cross-sectional enlargement 50 thereof. The holding projections 48, 48' are elastic, such that they radially clamp the bone screw 2 in the area of the cross-sectional enlargement 50 thereof.

The support 1 according to FIGS. 7a and 7b also has a height of 9.6 mm parallel to the axis of the receiving opening 17, a width of 5.9 mm parallel to the guide projections 15, and a length of 9.8 mm perpendicular to both of these directions.

A sixth embodiment of the support 1 according to the invention is shown in FIGS. 8a to 9c. According to the perspective view in FIG. 8a, the support 1 has a main body 23. A bone screw 2, of which only the head 9 can be seen here, is inserted in a receiving opening (not visible here). The support 1 and the bone screw 2 together form a unit 14.

Figure 8A:
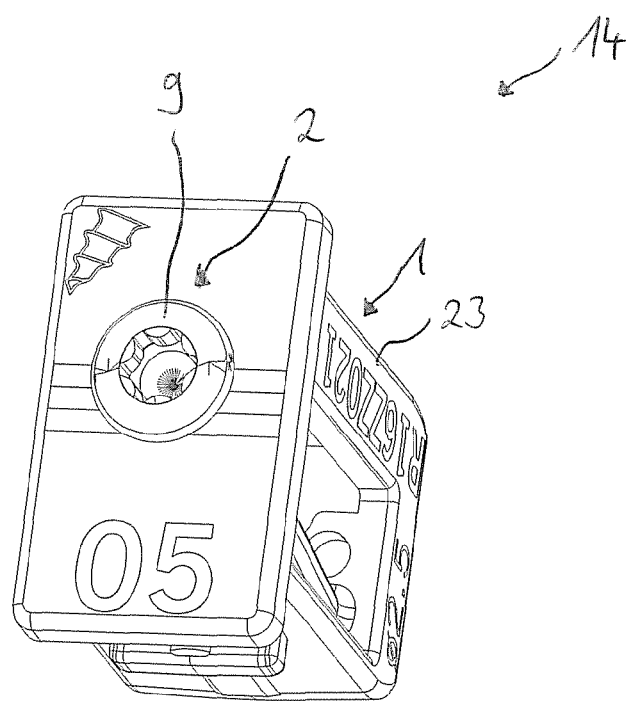
FIG. 8a shows a perspective view of a sixth embodiment of the support according to the invention, with a bone screw received therein.
Figure 8B:
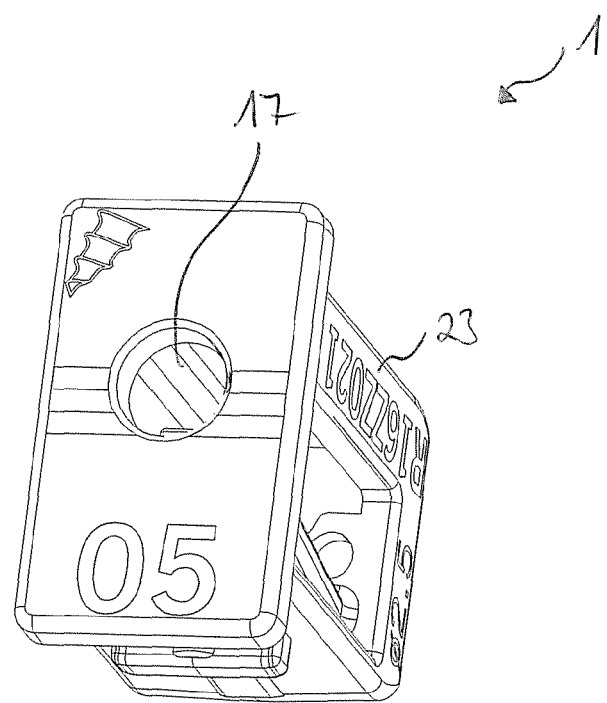
FIG. 8b shows a perspective view of the support according to the invention from FIG. 8a, without a bone screw.

FIG. 8b shows the same support 1 in the same perspective view, but without the inserted bone screw. The receiving opening 17 for the bone screw can be seen in this view.

FIG. 9a shows a side view of the support 1 according to FIGS. 8a and 8b. On each of two opposite sides, the support 1 has a respective guide projection 15. By means of these guide projections 15, the support 1 can be moved along a guide rail analogously to FIG. 4. In the receiving position A shown in FIG. 9a, a bone screw 2 is received by the support 1. The support 1 has a tongue 12, on the end of which a holding surface 4 is formed. In the receiving position A shown, this holding surface 4 is in contact with the bone screw 2, and this contact effects a first clamping force. This first clamping force has the effect that the bone screw 2 is held by the support 1.

In FIG. 9b, the unit 14 composed of support 1 and bone screw 2 is shown together with a screwdriver 41. The unit 14 comprising the support 1 and the bone screw 2 forms, together with the screwdriver 41, an osteosynthesis set according to the invention. The screwdriver 41 serves for the intended handling of the bone screw 2 and at the same time acts as a removal tool for the bone screw 2.

To reach the position shown in FIG. 9b, the screwdriver 41 was moved downward and thus brought into contact with the bone screw 2 in such a way that a second holding force acts between the blade 42 of the screwdriver 41 and the bone screw 2, which second holding force is greater than the first holding force. The second holding force is a second clamping force, which acts between a blade 42 of the screwdriver 41 and the head of the bone screw 2.

The force resulting from the first clamping force and from the second clamping force means that the bone screw 2 can be removed from the support 1 only by moving the screwdriver 41 in the removal direction E, as is shown in FIG. 9c. This greatly facilitates handling.

The supports 1 according to FIGS. 6a to 9c can, for example, comprise or be made of plastic and/or metal. They can be produced, for example, by selective laser sintering, milling, vacuum casting or injection molding.

FIG. 10 shows a first embodiment of a mounting 26 according to the invention, which can serve to fix at least one bone plate support for a bone plate on a base plate of a surgical container (cf. FIG. 14). The mounting 26 comprises a pin 30. The pin 30 extends along a longitudinal direction R, which is substantially perpendicular to a base plane G of the mounting 26. This base plane G can, for example, correspond to the plane of a base plate on which the mounting 26 is fixed for the intended use thereof. Along section planes lying perpendicularly with respect to the longitudinal direction R, the pin 30 is rectangular.

On each of two opposite sides 40, the pin 30 comprises in each case four equidistant locking projections 31. These locking projections 31 extend in a section plane lying perpendicularly with respect to the longitudinal direction R of the pin 30, i.e. parallel to the base plane G. The locking projections 31 thus form a cross-sectional widening.

The pin 30 has a height h of 20 mm along the longitudinal direction R and has, parallel to the base plane G, a width a of 4 mm and a thickness b of 4 mm also. The pin 30 can be made of stainless steel, for example, and be produced by milling or turning.

Figure 11:
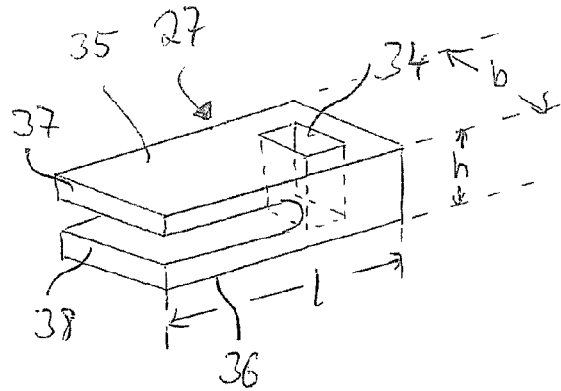
FIG. 11 shows a perspective view of a first embodiment of a bone plate support according to the invention.

FIG. 11 shows a perspective view of a first embodiment of a bone plate support 27 according to the invention. The bone plate support 27 has a plane upper face 35 and a plane lower face 36 arranged parallel to the upper face 35. Moreover, the bone plate support 27 has an opening 34, which pass right through the bone plate support 27 in a direction perpendicular to the upper face 35 and to the lower face 36. The bone plate support 27 also has an upper holding tongue 37 and a lower holding tongue 38, between which a bone plate can be clamped (cf. FIGS. 13a to 13d and 14). Here, the upper face of the upper holding tongue 37 forms part of the plane upper face 35 of the bone plate support 27, and the lower face of the lower holding tongue 38 forms part of the plane lower face 36 of the bone plate support 27.

The bone plate support 27 is elastic. It has a length l of 15 mm, a width b of 8 mm and a height h of 5 mm. The bone plate support 27 can be made, for example, of PPSU and be produced by injection molding.

Figure 12A:
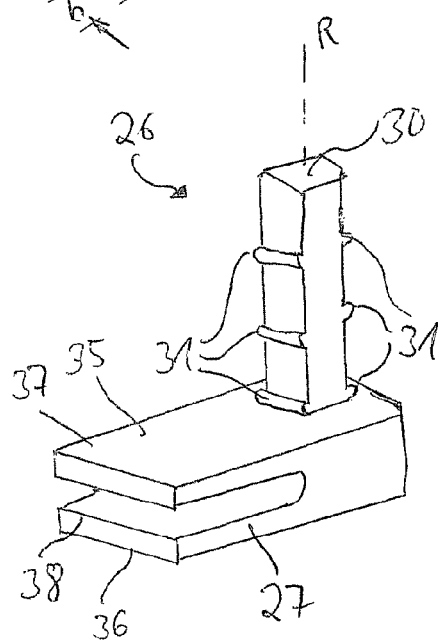
FIGS. 12a and 12b show perspective views of a system composed of a mounting according to FIG. 10, with one bone plate support in FIG. 12a and two bone plate supports in FIG. 12b.

FIG. 12a shows a mounting 26 with a bone plate support 27. The bone plate support 27 is placed with its opening 34 onto the pin 30 of the mounting 26. The bone plate support 27 is fitted onto the pin 30 in such a way that its upper face 35 lies below one of the locking projections 31 and its lower face 36 lies above the next down locking projection (not visible here). In this way, the bone plate support 27 is fixed releasably along the longitudinal direction R of the pin 30. Within the meaning of the invention, therefore, the locking projections 31 form fixing means, and the bone plate support 27 is FIG. 12a is located in a fixing position.

Because of its elasticity, the bone plate support 27 can be moved along the longitudinal direction R of the pin 30 when a certain force is applied and can be brought into another fixing position, which is likewise defined by two adjacent locking projections 31. Likewise, by application of a sufficient force, the bone plate support 27 can also be removed completely from the pin 30. However, the locking projections 31 ensure that the bone plate support 27 cannot accidentally slip off the pin 30, for example as a result of the mounting 26 being tilted.

Figure 12B:
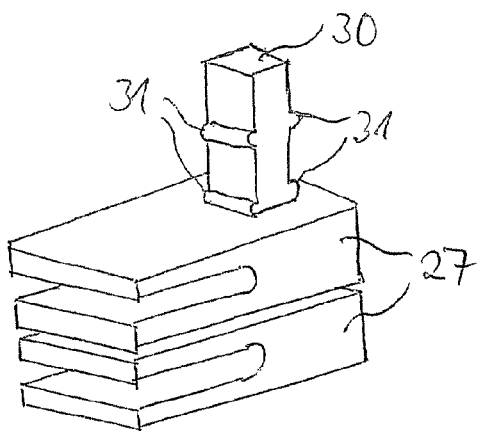
Figure 13A:
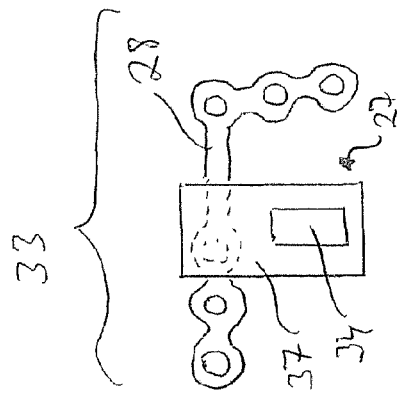
Figure 13B:
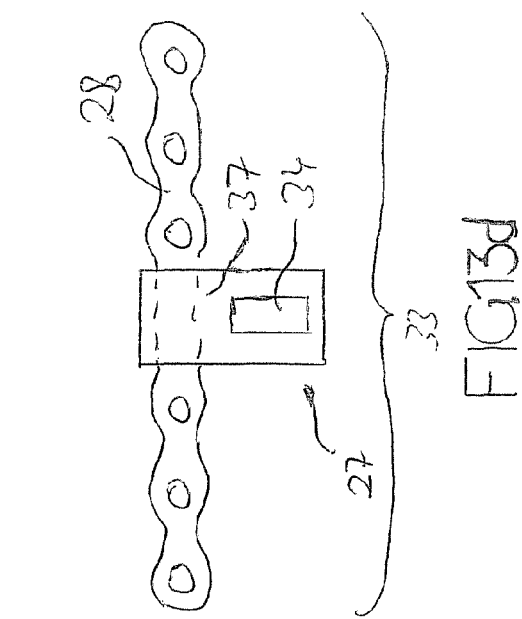
Figure 13C:
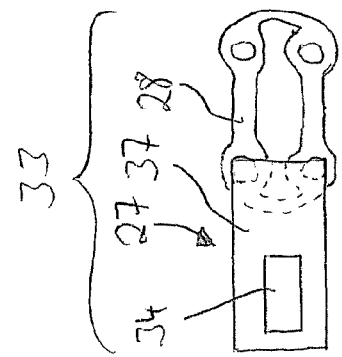
Figure 13D:
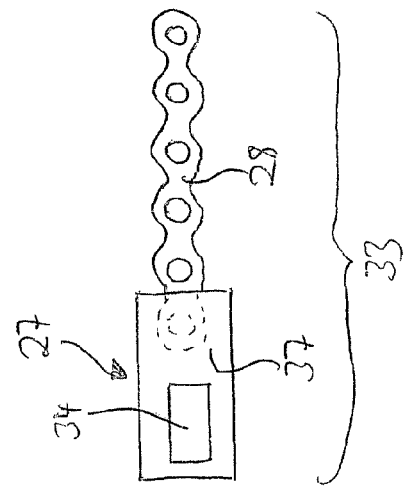

FIG. 12b shows the mounting 26 with two bone plate supports 27 stacked one on top of the other. The two bone plate supports 27 are located in two adjacent fixing positions, which are defined by the locking projections 31.

FIGS. 13a to 13d each show plan views of a unit 33 according to the invention composed of a bone plate support 27 and of one of four different bone plates 28. The bone plates 28 are in each case clamped between the upper holding tongue 37 and the lower holding tongue (not visible here) of the bone plate support 27.

FIG. 14 shows a surgical container 39 with a base plate 29. A mounting 26 according the invention as shown in FIG. 12 is fixed on the base plate 29. It can preferably be fixed on the base plate 29 by a screw (not visible here), which is guided from the underside of the base plate 29 through an opening in the base plate 29 and screwed into a hollow space of the pin 30 provided with an internal thread. Alternatively, the mounting 26 can also be fixed on the base plate 29 by adhesive bonding, a bayonet catch or a plug connection. The imaginary base plane G here coincides with the plane of the base plate 29. Several bone plate supports 27, each with a bone plate 28, are fitted onto the pin 30 of the mounting 26. Because of the locking projections 31 of the pin 30, the bone plate supports 27 cannot slip off the pin 30 even if the container 39 is tilted.

FIG. 15 shows a further mounting 26 according to the invention for fixing a plurality of bone plate supports. The mounting 26 has a pin 30, and a marking element 43 that can be connected releasably to the pin 30. The planar marking element 43 defines a base plane G of the mounting 26. In the assembled position, the pin 30 is oriented perpendicularly with respect to this base plane G (cf. also FIG. 17).

Along section planes lying perpendicularly with respect to the longitudinal direction R of the pin 30, the pin 30 has a cross section that has the shape of a circle segment with a circle segment angle α of 254°, for example. The pin 30 also has two locking recesses 56, which form a cross-sectional narrowing in a section plane perpendicular to the longitudinal direction R of the pin 30. The locking recesses 56 thus form fixing means, with the aid of which a bone plate support (not shown here) can be fixed in two different fixing positions along the longitudinal direction R (cf. FIGS. 17 to 19).

The marking element 43 has an opening 57, which is shaped as a segment of a circle and from which four slits 58 extend radially outward. The pin 30 can be releasably connected to the marking element 43 by being inserted into the opening 57. The slits 58 make this insertion easier.

The pin 30 can be made of stainless steel, for example, and can be produced by turning or milling. The marking element 43 can be made of plastic, for example, and can be produced by injection molding, cutting or punching. The marking element 43 has a thickness of 1 mm, a width of 16 mm and a length of 23.5 mm. The pin 30 has a height h of 14.1 mm.

FIGS. 16a and 16b show another bone plate support 27 according to the invention and a bone plate 28. The bone plate support has a substantially plane upper face 35, and a substantially plane lower face (not visible in FIG. 16a) arranged substantially parallel to the upper face 35. The bone plate support 27 also has an opening 34 passing right through it and delimited by three clamping tongues 47. Each of the three clamping tongues 47 has, in the area of its lower end, a fixing projection 59, which protrudes into the opening 34. By means of the clamping tongues 47 and the fixing projections, the bone plate support 27 is fixed releasably on the pin 30 of the mounting 26 according to FIG. 15 (cf. FIGS. 17 to 19).

The bone plate support 27 has an upper holding tongue 37 and a lower holding tongue 38, between which the bone plate 28 can be clamped (cf. FIG. 17). The upper face 35 of the bone plate support is formed by the upper face of the upper holding tongue 37, while the lower face 36 of the bone plate support 27 is formed by the lower face of the lower holding tongue 38. The lower holding tongue 38 has three holding projections 45 for holding the bone plate 28. These holding projections 45 extend perpendicularly with respect to the lower face 36 of the bone plate support 27.

FIG. 16b shows a side view of the bone plate support 27 and of the bone plate 28 from FIG. 16a. The lower face 36 of the bone plate support 27 can also be seen in this view. On its lower face, the upper holding tongue 37 has two abutments 44, each with an abutment surface 63 for positioning the bone plate 28. The abutment surfaces 63 extend perpendicularly with respect to the upper face 35 of the bone plate support 27. The upper holding tongue 37 also has, on its lower face, a holding surface 64 extending parallel to the upper face 35 of the bone plate support 27 (cf. also FIG. 16c). The bone plate 28, by being pushed in laterally, can be clamped between the holding surface 64 and the holding projections 45. The position of the bone plate 28 is defined by contact with the two abutment surfaces 63.

FIG. 16c shows a perspective view of the bone plate support 27 from below. As can be seen here, the two abutments 44 extend perpendicularly with respect to the upper face 35 of the bone plate support 27. The lower holding tongue 38 has two irrigation openings 46, which extend right through the holding tongue 38. A flushing medium, in particular a liquid or gaseous cleaning fluid, can pass through these irrigation openings 46.

FIG. 17 shows the mounting 26, composed of pin 30 and marking element 43, and also two bone plate supports 27, which each have a bone plate 28 and can be fitted onto the pin 30.

In the position shown in FIG. 18, these two bone plate supports 27 have been fitted, one on top of the other, onto the pin 30 of the mounting 26. The respective openings 34 of the bone plate supports 27 have been fitted onto the pin 30. The fixing projections 59 of the bone plate support 27 (cf. FIG. 16a) engage with the locking recesses 56 of the pin 30, in order to fix the bone plate support 27 releasably in different fixing positions.

FIG. 19 shows a surgical container 39, which contains a plurality of systems, each of them with a mounting 26 and with two units composed of a bone plate support 27 and of a bone plate 28. The mountings 26 are fixed on an apertured base plate 29 of the container 39. For this purpose, the pin 30 has a bore (not shown) along its longitudinal axis. The bore has an internal thread and is open in the direction of the bottom of the pin 30. The pin 30 has been fixed by being placed from above onto the base plate 29 and fixed with a fastening screw (also not shown), which has been guided from below through an opening in the base plate 29 and has been screwed into the internal thread of the bore. The marking element 43 has then been pushed over the pin 30 from above and locked relative thereto by means of a form-fit connection.

FIG. 20 shows a perspective view of another surgical container 39. This surgical container 39 contains mountings with bone plate supports 27 for bone plates 28, and also supports 1 with bone screws 2 received therein. In contrast to the container shown in FIG. 19, each pin 30 in this container 39 is fitted with four bone plate supports 27, each of these with a bone plate 28. The supports 1 are arranged movably along guide rails.

The invention claimed is:

1. A support for receiving at least one surgical object in a receiving position, said support comprising
   a main body, and
   at least one supporting surface, which is designed and arranged in such a way that a supporting area of the object can be brought into contact with the supporting surface in the receiving position, wherein the object can be removed from the receiving position in a removal direction, and the removal direction extends at an angle of at most 45° to a longitudinal axis of the object received in the receiving position, the support comprising at least one holding surface, which is movable relative to the main body and by which the object can be held in the receiving position wherein the support has at least two holding surfaces, which are movable relative to the main body and between which the object can be held, and/or the support has at least one holding surface, which is movable relative to the main body and has at least two holding surface portions between which the object can be held.

2. The support as claimed in claim 1, wherein the holding surface of the support is designed and arranged in such a way that the object in the receiving position can be held by means of the holding surface in a holding area that is arranged in the area of a shank of the object.

3. The support as claimed claim 1, wherein the supporting surface of the support is designed and arranged in such a way that, in the receiving position, it can be brought into contact with the underside of a cross-sectional enlargement of the object, which underside forms the supporting area.

4. The support as claimed in claim 3, wherein the object is a surgical fastener, with a head, which head forms the cross-sectional enlargement.

5. The support as claimed in claim 1, wherein the supporting surface and the holding surface are at a distance from each other in the removal direction.

6. The support as claimed in claim 1, wherein the object in the receiving position can be clamped by means of the holding surface in a clamping direction, which is substantially non-parallel to the removal direction.

7. The support as claimed in claim 1, wherein the support has at least two holding surfaces.

8. The support as claimed in claim 7, wherein the holding surfaces are arranged substantially uniformly around the longitudinal axis.

9. The support as claimed in claim 1, wherein the holding surface is pretensioned by spring means.

10. The support as claimed in claim 9, wherein the spring means comprise at least one tongue, of which the end comprises or forms the holding surface.

11. The support as claimed in claim 10, wherein, in the receiving position, at least the end of the tongue extends in a tongue direction, which forms an acute angle with the removal direction.

12. The support as claimed in claim 10, wherein the support contains an insert, which comprises:

a spring ring, which is arranged around the longitudinal axis, at least one of the tongues extending from the spring ring.

13. The support as claimed in claim 10, wherein at least part of the supporting surface is arranged at the end of the tongue.

14. The support as claimed in claim 1, wherein at least part of the supporting surface is arranged on the main body.

15. The support as claimed in claim 1, wherein the holding surface is designed and arranged in such a way that the object, in the receiving position, is substantially immovable in a direction different than the removal direction.

16. The support as claimed in claim 1, wherein the holding surface is designed and arranged in such a way that the object is movable in the removal direction by application of a first force, and, in a second direction different than the removal direction, is substantially immovable or is movable by application of a second force that is greater than the first force.

17. The support as claimed in claim 1, wherein the holding surface can be brought into a blocking position in which the object cannot be received in the support.

18. The support as claimed in claim 1, comprising connecting means for connecting the support to a storage unit.

* * * * *